United States Patent
Prieto et al.

(10) Patent No.: US 6,204,431 B1
(45) Date of Patent: *Mar. 20, 2001

(54) TRANSGENIC NON-HUMAN MAMMALS EXPRESSING HETEROLOGOUS GLYCOSYLTRANSFERASE DNA SEQUENCES PRODUCE OLIGOSACCHARIDES AND GLYCOPROTEINS IN THEIR MILK

(75) Inventors: Pedro A. Prieto, West Worthington; John J. Kopchick, Athens, both of OH (US); Richard D. Cummings, Edmond, OK (US); James M. Pierce, Athens, GA (US); David F. Smith, Athens, GA (US); Kelley W. Moremen, Athens, GA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/925,834

(22) Filed: Sep. 5, 1997

Related U.S. Application Data

(63) Continuation-in-part of application No. 08/208,889, filed on Mar. 9, 1994, now Pat. No. 5,750,176, and a continuation-in-part of application No. 08/715,259, filed on Sep. 16, 1996, now Pat. No. 5,892,070, which is a continuation of application No. 08/209,132, filed on Mar. 9, 1994, now abandoned, which is a continuation of application No. 08/434,151, filed on May 2, 1995, now Pat. No. 5,700,671, which is a division of application No. 08/209,132, filed on Mar. 9, 1994, now abandoned, and a division of application No. 08/433,271, filed on May 2, 1995, now Pat. No. 5,891,698, which is a division of application No. 08/209,122, filed on Mar. 9, 1994, now abandoned.

(51) Int. Cl.⁷ .................................................. A01K 67/027
(52) U.S. Cl. ................................... 800/14; 800/4; 800/6; 800/15; 800/16; 800/17; 800/18; 800/25
(58) Field of Search ................................. 800/14, 15, 16, 800/17, 18, 4, 7, 24, 6, 25; 435/69.1

(56) References Cited

U.S. PATENT DOCUMENTS

| | | |
|---|---|---|
| 5,032,519 | 7/1991 | Paulson et al. . |
| 5,047,355 | 9/1991 | Huber et al. . |
| 5,180,674 | 1/1993 | Roth . |
| 5,198,466 | 3/1993 | Picard et al. . |
| 5,322,775 | 6/1994 | Clark et al. . |
| 5,362,480 | 11/1994 | Au et al. . |
| 5,401,723 | 3/1995 | Gaffar et al. . |
| 5,565,362 | 10/1996 | Rosen . |
| 5,625,124 | 4/1997 | Falk et al. . |
| 5,700,671 * | 12/1997 | Prieto et al. ............. 435/172.3 |
| 5,891,698 * | 4/1999 | Prieto et al. ............. 435/67.1 |
| 5,892,070 * | 4/1999 | Prieto et al. ............. 800/2 |

FOREIGN PATENT DOCUMENTS

| | | |
|---|---|---|
| 0279582 | 8/1988 | (EP) . |
| 0502976 | 7/1996 | (EP) . |
| 0274489 | 10/1997 | (EP) . |
| 0396699 | 10/1997 | (EP) . |
| 58-10170 | 6/1983 | (JP) . |
| 8801648 | 3/1988 | (WO) . |
| 9203917 | 3/1992 | (WO) . |
| 9208692 | 5/1992 | (WO) . |
| 9315196 | 8/1993 | (WO) . |
| 9418986 | 9/1994 | (WO) . |
| 9500527 | 1/1995 | (WO) . |
| 9524488 | 9/1995 | (WO) . |
| 9524495 | 9/1995 | (WO) . |
| 9712892 | 4/1997 | (WO) . |
| 9718222 | 5/1997 | (WO) . |
| 9718790 | 5/1997 | (WO) . |

OTHER PUBLICATIONS

Kappell et al (1992) Current Opinion in Biotechnology 3, 548–553.*
Wall (1996) Theriogenology 45,57–68.*
Houdebine (1994) Journal of Biotechnology 34, 269–287.*
Fundamentals of Diary Chemistry, 2nd. Ed., Byron H. Webb et al, eds. Avi Publishing Co., Westport, CT, 1974, p. 43.*
Prieto, P.A. et al.; "Remodeling of mouse milk glycoconjugates by transgenic expression of a human glycosyltransferase" Journal of Biological Chemistry (Microfilms), vol. 270, No. 49, 1995, pp. 29515–29519, XP–002089594.
Chapter 19 of "The Science of Providing Milk for Man" by John R. Campbell and Robert T. Marshall, McGraw–Hill Book Company, New York, 1975, pp. 419–453.
USSN 07/226,445 (NTIS Order No. PAT.–APPL–7–226,445 (1988).
E. C. Adam et al., *Am. J. Respir. Crit. Care Med.*, vol. 155, (1997), pp. 2102–2104.
K. Baczako et al., *Journal of Pathology*, vol. 176, (1995), pp. 77–86.
T. Borén et al., *Science*, vol. 262, (1993), pp. 1892–1895.
T. Borén et al., *Trends In Microbiology*, vol. 2, No. 7, (1994), pp. 221–228.
R. D. Bremel et al., *J. Dairy. Sci.*, vol. 72, (1989), pp. 2826–2833.
T. Burdon et al., *Mechanisms of Development*, vol. 36, (1991), pp. 67–74.

(List continued on next page.)

Primary Examiner—Deborah Crouch
(74) Attorney, Agent, or Firm—Cheryl L. Becker

(57) ABSTRACT

The subject invention relates to methods of producing non-human transgenic mammals which produce various oligosaccharides and glycoconjugates in their milk. Additionally, the subject invention relates to the mammals themselves, the milk which they produce, compositions comprising the milk, fractions of the milk, and the purified oligosaccharides, as well as glyconjugates, present in the milk.

18 Claims, 26 Drawing Sheets

OTHER PUBLICATIONS

L. E. Cervantes et al., *Abstracts of the 97th General Meeting of the American Society for Microbiology*, (1997), pp. 117–118.

S. Eppenberger–Castori et al., *Glycoconjugate Journal*, vol. 6, (1989), pp. 101–114.

P. G. Falk et al., *Proc. Natl. Acad. Sci. USA*, vol. 92, (1995), pp. 1515–1519.

R. Freter et al., *Infection and Immunology*, vol. 14, No. 1, (1976), pp. 246–256.

R. A. Gaffney et al., *Infection and Immunology*, vol. 63, No. 7, (1994), pp. 3022–3026.

E. F. Grollman et al., *Biochemical and Biophysical Research Communications*, vol. 28, No. 1, (1967), pp. 50–53.

B. Guahathakurta et al., *J. Med. Microbiol.*, vol. 36, (1992), pp. 403–405.

Y. Ichikawa et al., *Analytical Biochemistry*, vol. 202, No. 2, (1992), pp. 215–238.

IUB–IUPAC, *The Journal of Biological Chemistry*, vol. 257, No. 7, (1982), pp. 3347–3351.

P. Jackson, *Biochemistry Journal*, vol. 270, (1990), pp. 705–713.

J. Jänne et al., *Ann. Med.* 24, (1992), pp. 273–280.

A. Kobata, *Methods In Enzymology*, vol. 28, No. 24, (1972), pp. 262–271.

A. Kobata et al., *Methods In Enzymology*, vol. 50, No. 21, (1978), pp. 216–226.

P. E. Kolenbrander et al., *Infection and Immunology*, vol. 57, No. 10, (1989), pp. 3204–3209.

P. Krimpenfort, *Cancer Detection and Prevention*, vol. 17, No. 2, (1993), pp. 301–305.

J. E. Kukowska–Latallo et al., *Genes and Development*, vol. 4, (1989), pp. 1288–1303.

R. D. Larsen et al., *Journal of Biological Chemistry*, vol. 265, No. 12, (1990), pp. 7055–7061.

R. D. Larsen et al., *Proceedings of the National Academy of Sciences*, vol. 86, (1989), pp. 8227–8231.

D. J. Legault et al., *Journal of Biological Chemistry*, vol. 270, No. 36, (1995), pp. 10987–10996.

J. B. Lowe et al., *Journal of Biological Chemistry*, vol. 266, No. 26, (1991), pp. 17467–17477.

I. Matsui et al., *J. Biochem.*, vol. 100, (1986), pp. 115–121.

E. McSweegan et al., *Infection and Immunity*, vol. 53, No. 1, (1986), pp. 141–148.

P. McVeagh et al., *J. Paediatr. Child Health*, vol. 33, (1997), pp. 281–286.

D. S. Newburg et al., *The Journal of Infectious Diseases*, vol. 162 (1990), pp. 1075–1080.

D. S. Newburg, *Journal of Nutrition*, vol. 127, No. 5, Suppl., (1997), pp. 980S–984S.

K. G. I. Nilsson, *Trends in Biotechnology*, vol. 6, (1988), pp. 256–264.

Y. Nishikawa et al., *Epidemiol. Infect.*, vol. 107, (1991), pp. 171–179.

T. F. Ørntoft et al., *Journal of Biological Chemistry*, vol. 271, No. 50, (1996), pp. 32260–32268.

S. Pal et al., *Med. Sci. Res.*, vol. 24, (1996), pp. 735–737.

A. Perry et al., *Infection and Immunity*, vol. 43, No. 1, (1984), pp. 257–262.

P. A. Prieto et al., *The Journal of Biological Chemistry*, vol. 270, No. 49, (1995), pp. 29515–29519.*

T. W. Rademacher et al., *Ann. Rev. Biochem.*, vol. 57, (1988), pp. 785–838.*

V. P. Rajan et al., *The Journal of Biological Chemistry*, vol. 264, No. 19, (1989), pp. 11158–11167.*

G. P. Reddy et al., *Analytical Biochemistry*, vol. 198, (1991), pp. 278–284.*

I. J. Rosenstein et al., *Infection and Immunity*, vol. 60, No. 12, (1992), pp. 5078–5084.*

A. Sarnesto et al., *Journal of Biological Chemistry*, vol. 265, No. 25, (1990), pp. 15067–15075.*

A. Sarnesto et al., *Journal of Biological Chemistry*, vol. 267, No. 4, (1992), pp. 2737–2744.*

A. Shamay et al., *Transgenic Research*, vol. 1, (1992), pp. 124–132.*

*Sigma Chemical Company Catalog*, (1992), p. 590.*

R. R. Townsend et al., *Glycobiology*, vol. 1, No. 2, (1991), pp. 139–147.*

J. Van Brunt, *Biotechnology*, vol. 6, No. 10, (1988), pp. 1149–1154.*

W. H. Velander et al., *Scientific American*, Jan., 1997, pp. 70–74.*

R. J. Wall et al., *Proc. Natl. Acad. Sci. USA*, vol. 88, (1991), pp. 1696–1700.*

K. D. Weinmeister et al., *Am. J. Crit. Care Med.*, vol. 150, (1994), pp. 131–134.*

I. Wilmut et al., *J. Reprod. Fert. Suppl.*, vol. 41, (1990), pp. 135–146.*

* cited by examiner

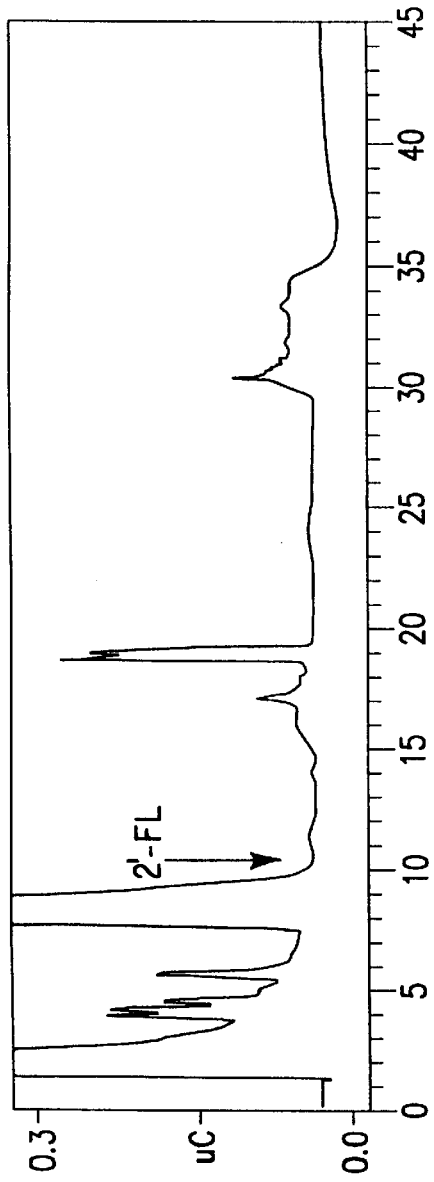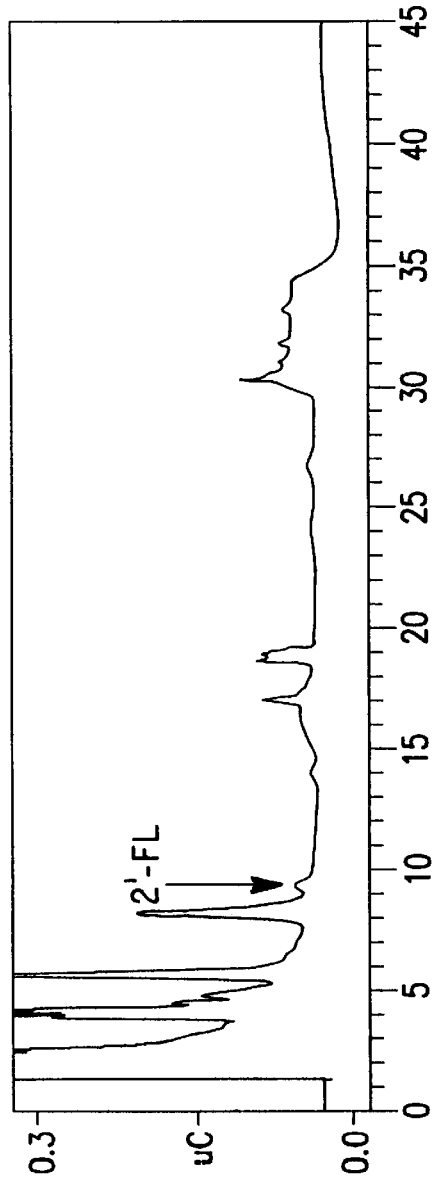

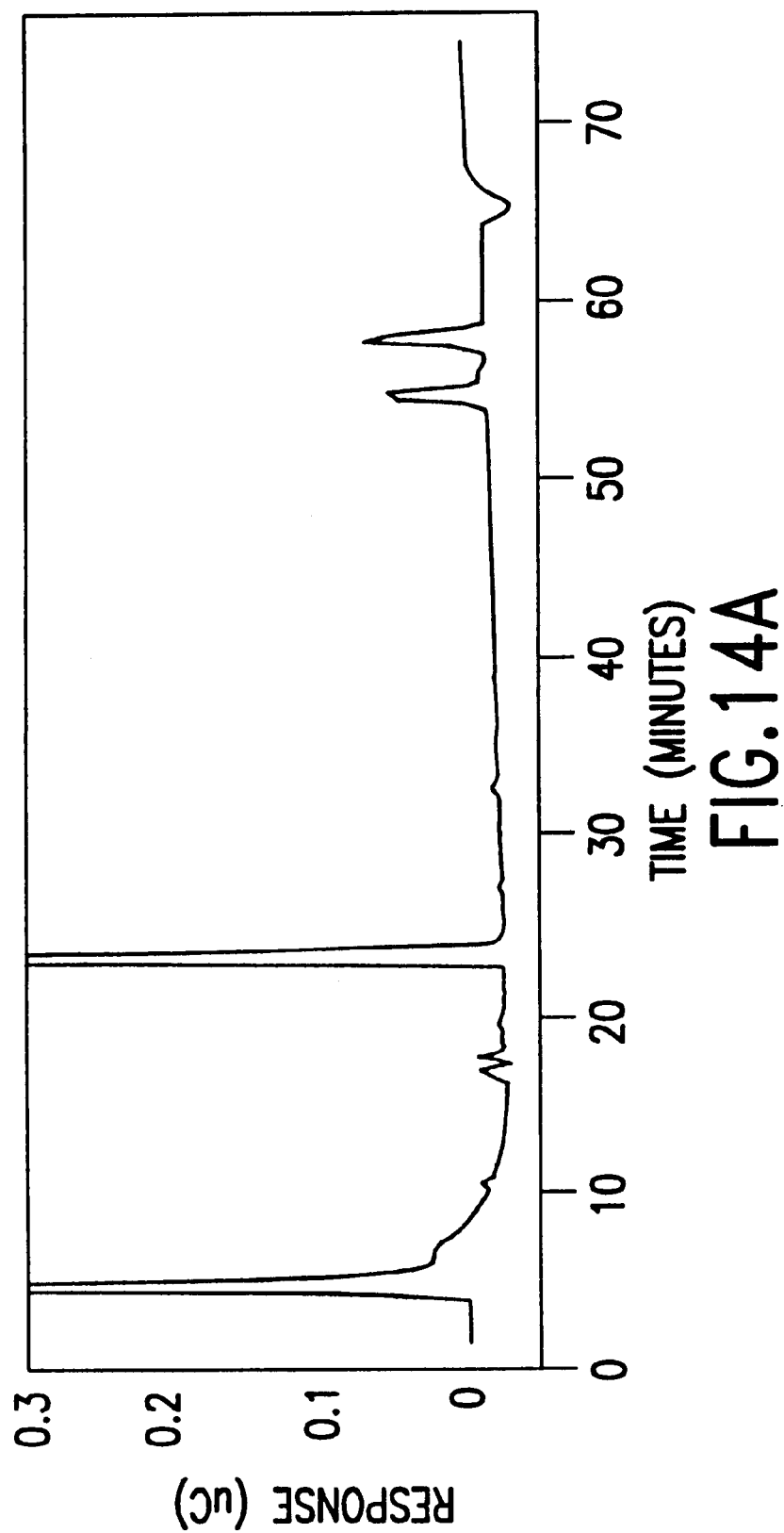

ated mammary secretory cells, a DNA sequence
TRANSGENIC NON-HUMAN MAMMALS EXPRESSING HETEROLOGOUS GLYCOSYLTRANSFERASE DNA SEQUENCES PRODUCE OLIGOSACCHARIDES AND GLYCOPROTEINS IN THEIR MILK The subject application is a continuation-in-part of U.S. patent application Ser. No. 08/208,889, filed Mar. 9, 1994, now U.S. Pat. No. 5,750,176, U.S. patent application Ser. No. 08/715,259, filed Sep. 16, 1996 now U.S. Pat. No. 5,892,070, which is a continuation of abandoned U.S. patent application Ser. No. 08/209,132, filed on Mar. 9, 1994, U.S. patent application Ser. No. 08/434,151, filed May 2, 1995 now U.S. Pat. No. 5,700,671, which is a divisional of U.S. patent application Ser. No. 08/209,132 abandoned, filed Mar. 9, 1994, and U.S. patent application Ser. No. 08/433,271, filed on May 2, 1995 now U.S. Pat. No. 5,891,698. which is a divisional of U.S. patent application Ser. No. 08/209,122, filed Mar. 9, 1994, abandoned, all of which are hereby incorporated in their entirety by reference.

BACKGROUND OF THE INVENTION

1. Technical Field

The subject invention relates to methods of producing non-human transgenic mammals which produce various oligosaccharides in their milk. Additionally, the subject invention relates to the generated mammals, the milk which these mammals produce, compositions comprising the milk, fractions of the milk, and the purified oligosaccharides, as well as glycoproteins, present in the milk.

2. Background Information

In the past, several individuals have achieved transgenic expression of primary gene products (i.e., proteins) in the milk of transgenic mammals (U.S. Pat. No. 5,322,775, Wall et al., *Proc. Natl. Acad. Sci. USA* 88:1696–1700 (1991) and Krimpenfort, P., *Cancer Detection and Prevention* 17(2):301–305 (1993)). Such expression was carried out in order to produce large quantities of the heterologous proteins in milk (Velander et al., *Scientific American,* January 1997, pp.70–74).

Recently, it was also demonstrated that expression of secondary transgenic products, for example, oligosaccharides, glycoproteins and glycolipids is, in fact, possible (Prieto et al., *Journal of Biological Chemistry* 49:29515–29519 (1995)). The experiments carried out by Prieto et al. advanced the concept of using the mammary glands of transgenic mammals as bioreactors and not solely as an alternative protein synthesis system.

Most of the experiments referenced in the above articles were carried out by expression of heterologous transgenes. One reason for such expression is because homologous genes, which are transgenically expressed, may cause difficulties, due to conflicts with internal protein synthesis of mammary gland development (Burdon et al., *Mechanisms of Development* 36:64–67 (1991)). Another reason why heterologous transgenes are utilized is that most of the experiments which have been carried out are designed for the production of human biological products.

The synthesis of secondary gene products, such as milk oligosaccharides, depends primarily on the expression of glycosyltransferases during lactation. Additionally, there are many benefits to the production of such oligosaccharides. For example, in a transgenic system for the synthesis of oligosaccharides, only catalytic amounts of glycosyltransferases are necessary. Also, the origin of the transgene may not be relevant as long as the secondary gene product or products are the desired one or ones.

It must also be noted that non-human mammals have a variety of glycosyltransferases which have counterparts in the human enzyme repertoire (Thurin et al., *The Journal of Biological Chemistry* 265(12):7055–7061 (1990)). Some of these transferases have been cloned from the tissues of non-human mammals, for example, mice (Larsen et al., *Proc. Natl. Acad. Sci. USA* 86:8227–8231 (1989)). Thus, transgenic expression of homologous glycosyltransferases in the mammary glands of non-human mammals represents a means of producing oligosaccharides, in addition to oligosaccharides produced using heterologous glycosyltransferases. Expression of both such enzyme types, as well as the oligosaccharides which are created by the action of such enzymes, and glycoproteins related thereto, are considered to fall within the scope of the present invention.

The oligosaccharides described above may be added, for example, to infant formula so that the formula-fed infant may receive the same benefits as the breast fed infant. For example, it is possible that the oligosaccharides may provide resistance to infection by pathogenic bacteria (Prieto et al., supra). Additionally, such oligosaccharides may be added to other compositions such as nutritional supplements or to pharmaceuticals. The aim of the present invention is to produce non-human transgenic mammals which produce such oligosaccharides, using either homologous or heterologous enzymes including, for example, glycosyltransferases. Such oligosaccharides may then be added to various compositions due to their beneficial properties.

Additionally, the presence of oligosaccharides and other glycoconjugates in the milk of transgenic animals may result in the acquisition of protection or resistance to viral, bacterial or fungal infections or toxins, by the offspring of such animals.

SUMMARY OF THE INVENTION

The present invention encompasses a method of synthesizing oligosaccharides and glycoproteins through transgenic expression of enzymes, for example, glycosyltransferases, during lactation. Furthermore, the invention also includes the production of oligosaccharide structures which are not present in nature. Such structures may be produced by transgenically expressing the appropriate eukaryotic or prokaryotic enzyme of interest, for example, a glycosyltransferase, in a mammal. Thus, the present invention allows for the production of homologous, heterologous and novel structures in the milk of transgenic mammals.

More specifically, the present invention encompasses a method for producing a non-human, transgenic mammal whose somatic and germ cells contain at least one transgene. Expression of the transgene results in the production of oligosaccharides and glycoproteins in the milk of the mammal. The method comprises the steps of: (a) preparing at least one transgene, (b) introducing the transgene or transgenes into a non-human, mammalian embryo, and transferring the resulting embryo into a recipient female, and then (c) identifying at least one female offspring. Expression of the transgene or transgenes results in the production of at least one enzyme which then catalyzes the production of oligosaccharides and glycoproteins in the milk of the mammal. Each transgene itself comprises, in operable association, at least one expression regulatory sequence functional in mammary secretory cells, a DNA sequence encoding a signal sequence functional in mammary secretory cells, and a DNA sequence encoding an enzyme. The non-human, transgenic mammal may be, for example, a mouse, a rat, a rabbit, a pig, a goat a sheep or a cow. The enzyme may be, for example, a glycosyltransferase such as a fucosyltransferase, a galactosyltransferase, an acetylase, a glucoronyltransferase, a gluconylepimerase, a sialyltransferase, a mannosyltransferase, a sulfotransferase, a β-acetylgalactosaminyltransferase or a N-acetylglucosaminyltransferase. Additionally, the oligosaccharides may be, for example, galactose α1-3 galactose β1-4 glucose, 2'fucosyllactose, 3'fucosyllactose, lacto-N-neo-tetraose, lacto-N-tetraose, lacto-N-fucopentaose, a sialylated derivative of lacto-N-fucopentaose, lacto-N-fucopentaose II, a sialylated derivative of lacto-N-fucopentaose II, lacto-N-fucopentaose III, a sialylated derivative of lacto-N-fucopentaose III, lacto-N-fucopentaose IV, a sialylated derivative of lacto-N-fucopentaose IV, lacto-N-fucopentaose V, a sialylated derivative of lacto-N-fucopentaose V, lacto-N-di-fucopentaose I, a sialylated derivative of lacto-N-di-fucopentaose, lacto-N-di-fucopentaose II, a sialylated derivative of lacto-N-di-fucopentaose II, lacto-N-hexaose, a fucosylated derivative of lacto-N-hexaose, sialyltetrasaccharide a, a fucosylated derivative of sialyltetrasaccharide a, sialyltetrasaccharide b, a fucosylated derivation of sialyltetrasaccharide b, sialyltetrasaccharide c or a fucosylated derivative of sialyltetrasaccharide c.

Additionally, the present invention includes a non-human, transgenic mammal. The genome of the mammal comprises at least one DNA sequence encoding an enzyme operatively linked to a mammary gland-specific promoter. Expression of the DNA sequence or sequences results in the production of oligosaccharides and glycoproteins in the milk of the mammal. The mammal, enzyme and oligosaccharides may be those recited above.

Furthermore, the present invention includes a method of producing milk in a non-human, transgenic mammal. The method includes (a) preparing at least one transgene, (b) inserting the transgene or transgenes into the non-human, transgenic mammal, and (c) milking the non-human, transgenic mammal in order to obtain the milk. The milk comprises the oligosaccharides and glycoproteins. Each transgene comprises, in operable association, a promoter functional in mammary secretory cells and a DNA sequence encoding an enzyme. Expression of each transgene results in production of oligosaccharides and glycoproteins in the milk of the mammal. The mammal, enzyme and oligosaccharides may be, for example, those recited above.

Furthermore, the present invention encompasses a milk produced by a non-human, transgenic mammal. The genome of the non-human, transgenic mammal comprises at least one DNA sequence encoding an enzyme. The DNA sequence is operatively linked to a promoter. Expression of each DNA sequence results in the ultimate production of oligosaccharides and glycoproteins. Again, the mammal, enzyme and oligosaccharides may be, for example, those recited above.

Moreover, the present invention also includes a fraction of the milk described above. This fraction may include, for example, one or more of the soluble oligosaccharides and/or glycoconjugates produced as a result of expression of the transgene or transgenes. Thus, a fraction of the milk may comprise one or more of the above components (i.e., oligosaccharides or glycoconjugates) or any combination thereof. Such a fraction may also include oligosaccharides naturally occurring in the milk of the transgenic mammal in combination with one or more of the oligosaccharides and/or glycoconjugates produced as a result of the presence of the transgene or transgenes.

Additionally, the present invention encompasses an oligosaccharide or glycoprotein purified from the milk described above, as well as a nutritional product containing the milk, a fraction thereof, or the oligosaccharides and/or glycoproteins, all of which have been described above. This nutritional product may be an infant formula in either liquid or solid form.

The present invention also includes a method of providing nutrition to patients. This method comprises administering to the patients the milk, fraction thereof, or oligosaccharides or glycoproteins, all described above, in an amount sufficient to effect the nutrition.

BRIEF DESCRIPTION OF THE DRAWINGS

FIG. 1 illustrates the creation of the PWAP-GT construct.

FIG. 2 illustrates chromatographic analysis of galactose α1-3 galactose β1-4 glucose, a novel oligosaccharide produced by one of the methods of the present invention.

FIG. 3 represents fluorophore assisted carbohydrate electrophoresis (FACE) analysis of galactose α1-3 galactose β1-4 glucose.

FIG. 4 represents FACE analysis of mouse milk spiked with galactose α1-3 galactose β1-4 glucose.

FIG. 5 illustrates an example of a negative transgenic, positive transgenic, and negative control mouse milk oligosaccharide profile, as analyzed using Dionex Method 2. The large peak eluting at 31–32 minutes is presumed to be the trisaccharide.

FIG. 6 represents FACE analysis of the samples used in FIG. 5. In particular, FACE analysis was carried out in order to verify that the "new" peak detected in FIG. 5 was the trisaccharide. The band that runs concurrent with the G3 starch hydrolysate standard band is, indeed, the trisaccharide.

FIG. 7 illustrates the High pH, Anion Exchange Chromatography (HPAEC) oligosaccharide profiles of two rabbit milk samples. Panel A is the milk oligosaccharide profile of a sample obtained from a control, non-transgenic animal. This sample contains lactose and only trace amounts of 2'-fucosyllactose (Fucal-2Galβ1-4Glc). Panel B is the profile of a sample obtained from a lactating rabbit whose genome contained a transgene encoding human H-α1-2fucosyltransferase. This sample contains quantifiable 2'-fucosyllactose and has less than one-tenth of the lactose concentration present in the milk sample of the non-transgenic animal. Panel C is the profile obtained from the same sample used to generate the profile in Panel B but after the sample was spiked with 20 mg/liter of 2'-fucosyllactose.

FIG. 8 represents the ion chromatographic profiles of additional transgenic rabbit milk samples. Panel A is control milk, panel B is transgenic sample #2, panel C is transgenic sample #3, and panel D is transgenic sample #4. Only sample #4 (panel C) contained significant quantities of 2'-fucosyllactose (i.e., >50 mg/L). Sample #3 (panel B) exhibited a marked decrease in its lactose concentration.

FIG. 9 illustrates Fluorophore Assisted Carbohydrate Electrophoresis (FACE) of milk oligosaccharides before and after digestion with α1-2fucosyllactose from untreated and enzyme controlled rabbit milk, transgenic rabbit milk and an authentic standard. In particular, lane 1 represents authentic 2'fucosyllactose standard, lane 2 represents untreated transgenic sample #5, lane 3 represents the fucosidase-treated transgenic sample #5, lane 4 represents an untreated, non-transgenic control sample, and lane 5 represents the fucosidase treated control sample. Lane 6 represents a set of linear glucose polymer standards where G2 represents two glucose units, and G3 represents three glucose units.

FIG. 10 represents FACE of additional transgenic rabbit samples. In particular, lane 1 represents authentic 2'fucosyllactose standard, lane 2 represents untreated transgenic sample #5, lane 3 represents an additional transgenic milk sample, lane 4 represents transgenic sample #4, lane 5 represents a non-transgenic control sample, lane 6 represents a set of linear glucose polymer standards, and lane 7 represents transgenic sample #3.

FIG. 11 illustrates a Ulex Europaeus Agglutinin I (UEA-1) Western blot of transgenic and control rabbit milk proteins. Lane 1 represents a non-transgenic control sample, lane 2 represents transgenic sample #1, lane 3 represents transgenic sample #2, lane 4 represents the second non-transgenic control.

FIG. 12 represents a UEA-1 Western blot of the additional rabbit milk protein samples. Lane 1 is from a non-transgenic control, lane 2 is transgenic sample #4, lane 3 is transgenic sample #3, lane 4 is a non-transgenic control sample, and lane S represents molecular weight standards.

FIG. 13 illustrates a Coomassie stained SDS electrophoretogram in which rabbit milk proteins have been resolved. Lane 1 shows stained proteins from milk of a non-transgenic control, lane 2 is transgenic sample #3, lane 3 is transgenic sample #4, lane 4 is transgenic sample #5, and lane S Shows stained molecular weight standards.

FIG. 14 illustrates chromatographic profiles of milk oligosaccharide extracts. Panel A represents the control oligosaccharide extract, panel B represents the transgenic milk oligosaccharide extract, and panel C represents the spiked (i.e., 3-fucosyllactose) transgenic milk oligosaccharide extract.

FIG. 15 represents the FACE results of a gel electrophoresis used to resolve fluorophore-labeled oligosaccharides. Lane 1 is a labelled starch hydrolyzate used as a molecular weight standard, lane 2 is the neutral profile obtained from the milk of a non-transgenic control animal, lane 3 is authentic 3-fucosyllactose, lane 4 is the neutral profile of a transgenic animal expressing FucT-IV, and lane 5 is the same material as in lane 4 but after specific fucosidase digestion.

FIG. 16 illustrates FACE of selected fractions from control and transgenic milk oligosaccharide extracts after high pH anion exchange chromatography. Panel A represents a transgenic milk sample, and Panel B represents a non-transgenic control. Lane 1 of the gel represents dye, lane 2 represents transgenic oligosaccharide extract (fraction eluting at 19.5 minutes), lane 3 represents transgenic oligosaccharide extract (fraction election at 20.0 minutes), lane 4 represents transgenic oligosaccharide extract (fraction eluting at 20.5 minutes), lane 5 represents authentic 3-fucosyllactose, lane 6 represents control oligosaccharide extract (fraction eluting at 20.0 minutes), and lane 7 represents control oligosaccharide extract (fraction eluting at 20.5 minutes) and lane 8 represents the oligo ladder standard.

FIG. 17 is a chromatogram of the milk oligosaccharide profile obtained from a control, non-transgenic mammal.

FIG. 18 is a chromatogram of milk obtained from a transgenic mammal expressing the human Fuc α1-2-transferase and the murine Galα1-3 transferase.

FIG. 19 shows the chromatogram obtained from the enzyme activity assay of a control L-cell plate.

FIGS. 20 and 21 show the oligosaccharide synthesized by transfected L cells expressing the bacterial N-acetylglucosaminyltransferase.

DETAILED DESCRIPTION OF THE INVENTION

Figure 1:
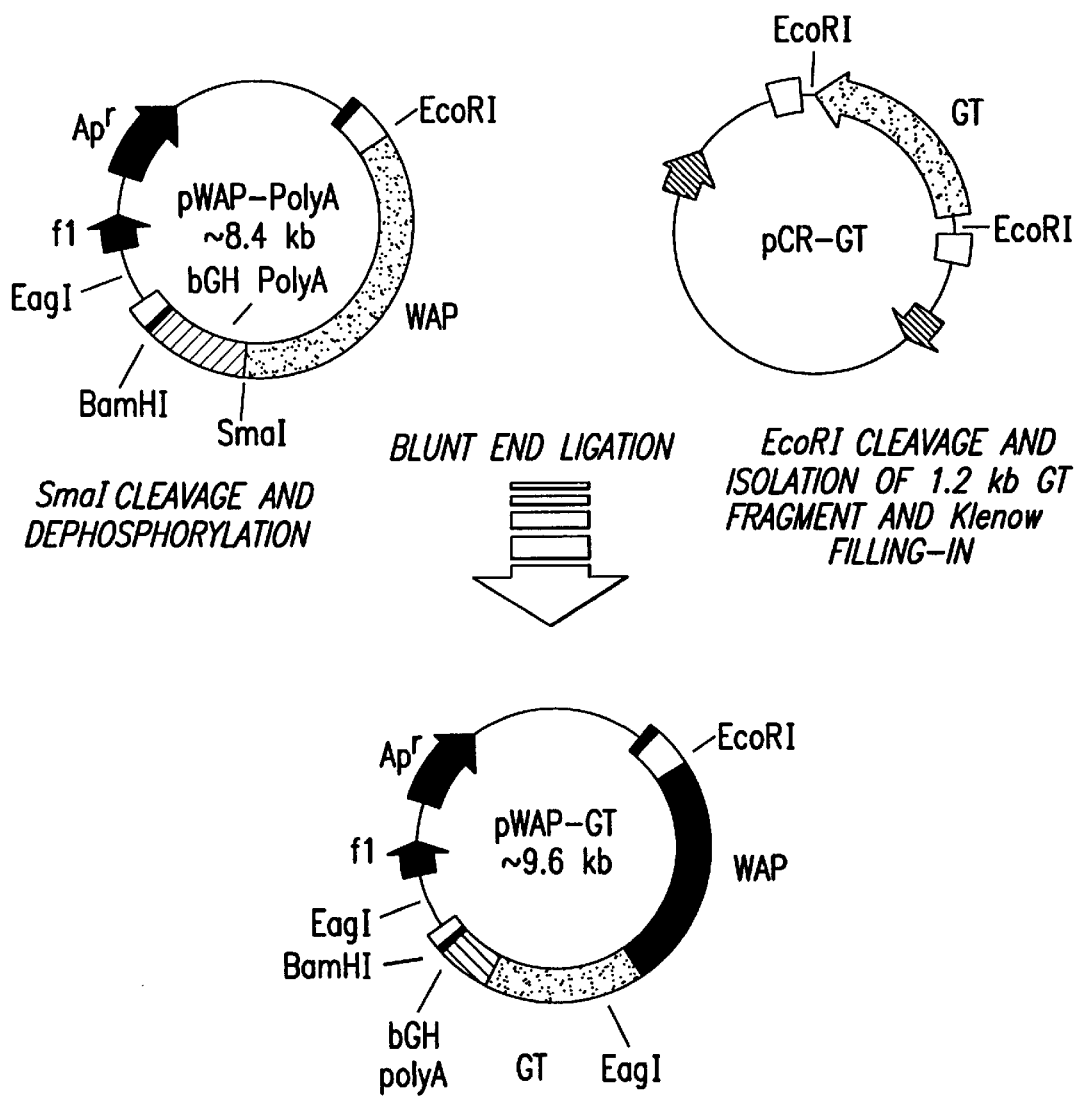
FIGS. 1–6 relate to a method involving expression of a homologous enzyme (i.e., murine UDP-Galβ-D-α1,3-galactosyltransferase).

As noted above, the subject invention relates to a method of producing one or more oligosaccharides and/or glycoconjugates in the milk of non-human transgenic mammals by the use of transgenic technology. One of the oligosaccharides which may be produced by the method of the invention (i.e., galactose α1-3 galactose β1-4 glucose) has a novel structure and has never been reported to exist as a free oligosaccharide. Such transgenically produced oligosaccharides and/or glycoconjugates, produced according to the present invention, may be added to infant formulas or to medical nutritionals given to the elderly or to immunocompromised patients. The presently described method and variants thereof have the benefit of allowing scientists to custom design milk oligosaccharide profiles of transgenic animals.

Briefly, in order to produce the desired milk oligosaccharide or oligosaccharides, a segment of DNA encoding a particular enzyme of interest is isolated from a particular eukaryotic or prokaryotic species. This enzyme is responsible for the production of the secondary gene product or milk oligosaccharide. Subsequent to isolation, the DNA segment is inserted into a vector containing various genetic components such as, for example, a polyadenylation signal and a promoter. A portion of the vector containing the required components is then inserted into the pronucleus of an embryo of the same or of a different mammalian species from which the DNA segment was isolated. The embryo is then implanted into a recipient female, and birth is allowed to occur. Milk samples from the offspring contain the oligosaccharide or oligosaccharides of interest. Subsequent generations are also monitored for production of the oligosaccharide or oligosaccharides and thus incorporation of the gene or genes encoding the enzyme or enzymes of interest into their genomes. It should be stressed that more than one transgene may be introduced into the embryo thereby leading to production of more than one oligosaccharide. Thus, the potential of the present invention is endless. Each step of the present method is described in detail below.

The Enzyme

The enzyme of interest, which is ultimately expressed, is chosen based upon the oligosaccharide or oligosaccharides one wishes to produce in the milk of the non-human transgenic mammal. The enzyme may be, for example, a glycosyltransferase. A suitable glycosyltransferase includes, for example, a fucosyltransferase such as α-1,2-fucosyltransferase, fucosyltransferase IV or "H" fucose α-1, 2-transferase, a galactosyltransferase such as gal α-1-3 transferase, an acetylase, a glucoronyltransferase, a glucosylepimerase, a sialyltransferase, a mannosyltransferase, a sulfotransferase, a β-acetylgalactosaminyltransferase and a N-acetylglucosaminyltransferase. The enzyme of choice is preferably a galactosyltransferase, and more preferably UDP-Gal B-D-α1,3 galactosyltransferase, a sialyltransferase, or a α1-3/4 fucosyltransferase such a FucT-III or FucT-IV.

The glycosyltransferases encoded by the transgenes are targeted by signal sequences, either naturally encoded by cDNA or genomic DNA or which are added using standard genetic engineering techniques. They may be present in the lactogenic cells of the transgenic animals and may be either anchored to intracellular membrane compartments (e.g., endoplasmic reticulum, golgi apparatus or secretory vesicles) of lactogenic cells or may exist as free catalytic polypeptides in the lumen of such compartments. Through appropriate intracellular localization, the enzymes have access to sugar nucleotides or other sugar donors synthesized naturally by the lactating mammary gland cells or may obtain access to such cells from the bloodstream of the animal. These donors are preferably sugar nucleotides.

The glycosyltransferases have the ability to catalyze the transfer of monosaccharide units from the sugar donors to acceptors such as lactose, other oligosaccharides, glycolipids or glycoproteins. The glycosyltransferases may have limited or ample specificity for both donors and acceptors and may act by transferring more than one monosaccharide unit to a nascent or elongating glycoconjugate. Thus, larger oligosaccharides and/or polysaccharides can be synthesized by the reiterative or iterative action of the glycosyltransferases. The glycosytransferases may themselves be glycoproteins or non-glycosylated glycoproteins or may or may not have additional co- and post-translational modifications.

It is important to note, again, that an oligosaccharide profile of a transgenic mammal can be designed based upon choice of one or more appropriate enzymes which result in production of the oligosaccharides and glycoproteins of choice.

Furthermore, it should also be noted that the present invention allows for simultaneous expression of two or more enzymes and thus corresponding oligosaccharides and glycoproteins. Thus, potentially, a non-human transgenic mammal, for example, a cow, could be created which had the ability to produce many oligosaccharides present in human breast milk. The oligosaccharides could then be added to infant formula, for example, thereby providing the formula fed infant with the oligosaccharide-derived benefits received by the breast fed infant. Mammals, such as the cow described above, could then be allowed to mate (i.e., crossbred) in order to obtain offspring which have the ability to produce a wide variety of valuable oligosaccharides in their milk.

Additionally, the present invention also encompasses the production of enzymes (e.g., glycosyltransferases) from invertebrates. Such invertebrates include, for example, *Schistosoma mansonii* or bacteria, such as from the Neisseriae genus. These enzymes may be expressed in active form in mammalian tissues during lactation.

The Non-Human Transgenic Mammal

A mammal, from which the cDNA encoding the enzyme of interest may be isolated is selected from the group consisting of, for example, a mouse, a rat, a rabbit, a pig, a goat, a sheep, a horse and a cow. However, any mammal may be utilized provided it has the ability to incorporate DNA encoding the enzyme of interest into its genome.

The embryo into which the cDNA is inserted may or may not correspond to the same species from which the DNA was initially isolated, depending upon whether heterologous expression or homologous expression of the enzyme is desired. More specifically, if one desires, for example, to produce a human enzyme which, in turn, leads to the production of a human oligosaccharide in the milk of a non-human, transgenic mammal (i.e., heterologous expression of the enzyme), the transgenic mammal utilized is a non-human mammal such as, for example, a pig or a goat. However, if one wishes to produce, for example, a goat enzyme which, in turn, leads to the production of at least one oligosaccharide in the milk of a goat (i.e., homologous expression of the enzyme), the transgenic mammal utilized will be a goat.

With regard to homologous expression, the present invention allows one to synthesize oligosaccharides that are not present in nature such as, for example, galactose α1-3 galactose β1-4 glucose, as well as all naturally occurring oligosaccharides. Furthermore, the present invention allows for analysis of the synthesis efficiency of the enzyme encoded by the gene of interest. Also, since the enzyme is "native" to the mammal (i.e., derived from the same species), the potential of a self-immune reaction to the enzyme or intolerance in milk-fed progeny are reduced. Additionally, since some enzymes (e.g., glycosyltransferases) are found in some species and not others, the spectrum of potential oligosaccharides which may be transgenically synthesized in milk is increased by using available genes encoding homologous enzymes.

Also, with respect to homologous expression, it should be noted that homologous glycosyltransferase, for example, may be obtained and cloned from tissues other than the lactating mammary gland. For example, a murine glycosyltransferase which is normally expressed in liver and in other tissues, but is not expressed in lactating mammary glands of mice, may be expressed during lactation through the action of a lactogenically responsive promoter. The secondary gene products (i.e., oligosaccharides and glycoconjugates) will be present in the milk of the transgenic mice. Thus, as evidenced in Example I below, it is possible to synthesize oligosaccharides that are not normally synthesized by the lactating mammary gland of a given mammal as long as a glycosyltransferase, which is normally expressed in other tissues, is transgenically expressed in the lactating mammary gland.

The Vector

The entity into which the cDNA (encoding the enzyme) is initially inserted is referred to a vector. The vector may be, for example, a bacterial plasmid (e.g., pBR-322). If a bacterial plasmid is used, it should contain at least a recombinant DNA sequence which directs gene expression and protein synthesis, preferably during lactation, either a cDNA, gene or gene fragment encoding at least one glycosyltransferase, and a DNA sequence encoding a polyadenylation addition site required for proper messenger RNA processing. Alternatively, the vector may be constructed using other plasmids, cosmids, phage DNA, viruses and other vectors specific for yeast, plant, mammalian and other suitable hosts.

The promoter, which regulates expression of the cDNA, gene or gene fragment encoding the enzyme and which is operably linked thereto, may be, for example, lactalbumin, casein, whey acidic protein (WAP) or another lactogenic promoter.

The polyadenylation signal may be, for example, a mammalian or viral signal including, for instance, the poly-a signal of SV-40T-antigen, ovalbumin or bovine growth hormone (bGHpdyA).

Oligosaccharides

Oligosaccharides which may be produced according to the method of the present invention include, for example, galactose α1-3 galactose β1-4 glucose, 2'fucosyllactose, 3'fucosyllactose, lacto-N-neo-tetraose, lacto-N-tetraose, for example, α-lacto-N-tetraose, lacto-N-fucopentaose I and its sialylated derivatives, lacto-N-fucopentaose II and its sialylated derivatives, lacto-N-fucopentaose III and its sialylated derivatives, lacto-N-fucopentaose IV and its sialylated derivatives, lacto-N-fucopentaose V and its sialylated derivatives, lacto-N-di-fucopentaose I and its sialylated derivatives, lacto-N-di-fucopentaose II and its sialylated derivatives, lacto-N-hexaose and its fucosylated derivatives, sialyltetrasaccharide a, b, and c and their fucosylated derivatives, other human milk and non-human milk oligosaccharides.

Galactose α1-3 galactose β1-4 glucose and α1-2-fucosyllactose are produced in the examples. The former compound represents the first novel, undescribed secondary gene product synthesized by transgenic technology. In particular, galactose α1-3 galactose β1-4 glucose has never before been shown to exist in nature as a free oligosaccharide until the present invention. It is thought that this oligosaccharide may be used, for example, as an agent to induce tolerance to Galα1-3 antigen in humans prior to xenotransplantation of non-human animal organs suchs as heart, liver and kidney.

It must be noted that the present invention encompasses the milk produced by the non-human transgenic mammal which contains one or more of the above oligosaccharides. Additionally, however, the present invention also includes fractions of the milk as well as the oligosaccharides and glycoconjugates (e.g., glycoproteins) isolated or purified from the milk. Such fractions may include, for example, solids of the milk, delipilidated or skim milk, milk from which the cream or lipids have been removed, the soluble carbohydrate fraction (i.e., specific oligosaccharides either alone or in combination with the mammal's naturally produced carbohydrates) and/or specific glycoconjugates or groups of glycoconjugates. Such fractions may be obtained by methods known to those of ordinary skill in the art, for example, evaporation, lyophilization, crystallization, ultrafiltration, dialysis, or chromatography, (e.g., affinity, anion exchange or gel exclusion).

Additionally, the present invention includes glycoconjugates (e.g., human milk proteins and human serum proteins) which are modified as a result of the action of the transgenically expressed enzymes. Such glycoconjugates may be endogenous or transgenically expressed. Examples of human milk proteins (i.e., glycoproteins) which may undergo modification include secretory immunoglobulins, lysozyme, lactoferrin, kappa-casein, alpha-lactalbumin, beta-lactalbumin, lactoperoxidase and bile salt stimulated lipase. The enzyme may, for example, add a linkage to the glycoprotein which would not be present naturally in the glycoprotein (see Prieto et al., *Journal of Biological Chemistry* 270:29515–29519 (1995)). Thus, the glycoprotein acts as a substrate for the enzyme.

It should be noted that either homologous or heterologous glycoproteins can be expressed transgenically in mammals which are already expressing transgenes encoding glycosyltransferases. Thus, direct glycosylation may result, for example, from the action of endogenous as well as the transgenically expressed glycosyltransferases.

The present invention may be illustrated by the use of the following non-limiting examples:

The following reagents and equipment were required for use in Example I:

REAGENTS:
1) 500 mM sodium hydroxide and 200 mM sodium hydroxide, RICCA Chemical Company (Arlington, Tex.), carbonate free, National Institue of Standards and Technology (NIST)-traceable (Baxter Inc., McGaw Park, Ill.);
2) Sodium acetate, ACS grade (Sigma, St. Louis, Mo.);
3) FACE reagent kit (Glyko Inc., Novato, Calif.);
4) Milli-Q water (Millipore, Bedford, Mass.); and
5) Sulfuric Acid Ultrex Ultrapure Grade (Baxter).

EQUIPMENT:
Sample Drying: All samples and standards were dried using a Speed Vac Plus SC210A equipped with a Refrigerated Vapor Trap RVT4104 (Savant, Farmingdale, Ill.).

EXAMPLE I

Expression of Murine UDP-Galβ-D-α1,3 Galactosyltransferase (Homologous Expression)

A. Preparation of Plasmid and Creation of Transgenic Mouse Embryos

The genetic construct was prepared at the Edison Biotechnology Institute at Ohio University (Athens, Ohio). A cDNA encoding the murine UDP-Gal:β-D-Galα1,3 galactosyltransferase was inserted into a plasmid containing the polyadenylation signal of bovine growth hormone (bGHpolyA) and the lactogenically-responsive murine whey acidic protein (WAP) promoter (see FIG. 1). An EcoRI-BamHI fragment was microinjected into the pronuclei of mouse embryos. The presence of the gene was detected by tail slot blots. Milk from lactating females was collected and stored frozen at −70° C. until shipped to Ross Labs for carbohydrate analysis.

B. High Performance Anion Exchange Chromatography Analysis of Oligosaccharides of A Mouse milk oligosaccharide standards were analyzed using a Dionex Bio-LC System, equipped with the following:

Pump: Dionex Advanced Gradient Pump

Detector: Dionex Pulsed Electrochemical Detector with gold working electrode and pH/reference electrode Autosampler: Spectrophysics Refrigerated AS3500

Columns: Method 1: 1 Dionex CarboPac PA1 analytical column (4×250 mm) preceded by a guard (4×50 mm)
Method 2: 2 Dionex CarboPac PA1 analytical columns (4×250mm each, connected in serial) preceded by a guard (4×50 mm)

Chemical Suppression: Dionex AMMS-II Anion Micromembrane Suppression, (installed after detector but before fraction collector, used to neutralize samples), regenerated by 0.15% sulfuric acid using Dionex AutoRegen Apparatus and Anion Regenerate Cartridge Fraction Collector: BioRad Model 2110 (BioRad Inc., Hercules, Calif.)

All equipment was purchased from Dionex, Inc. (Sunnyvale, Calif.) unless otherwise noted. Eluants used were a combination of (A) Milli-Q water (or equivalent), (B) 500 mM sodium hydroxide, (C) 600 mM sodium acetate in 100 mM sodium hydroxide, and/or (D) 200 mM sodium hydroxide, at a flow rate of 1.0 ml/min. Table I below contains the eluant profiles for the two methods used. Detector settings are as listed in Table II below. Injection volume was 20 μl.

Dionex Analysis of Samples and Standard: All samples, and/or standards were analyzed as prepared without further dilution.

TABLE I

Eluant Profiles

| Method 1: | | | | | Method 2: | | | | |
|---|---|---|---|---|---|---|---|---|---|
| Time (min) | % A | % B | % C | % D | Time (min) | % A | % B | % C | % D |
| 0.0 | 50 | 0 | 0 | 50 | 0.0 | 99 | 1 | 0 | 0 |
| 12.0 | 50 | 0 | 0 | 50 | 60.0 | 0 | 100 | 0 | 0 |
| 12.1 | 46 | 0 | 7 | 47 | 60.1 | 99 | 1 | 0 | 0 |
| 20.0 | 46 | 0 | 7 | 47 | 75.0 | 99 | 1 | 0 | 0 |
| 20.1 | 45 | 0 | 10 | 45 | | | | | |
| 27.0 | 45 | 0 | 10 | 45 | | | | | |
| 27.1 | 25 | 0 | 50 | 25 | | | | | |
| 32.0 | 25 | 0 | 50 | 25 | | | | | |
| 32.1 | 50 | 0 | 0 | 50 | | | | | |
| 59.0 | 50 | 0 | 0 | 50 | | | | | |

A = Milli-Q Water
B = 500 nM NaOH
C = 600 mM NaOHAc/100 mM NaOH
D = 200 mM NaOH

TABLE II

Detector Settings

| Integration Parameters: | Method 1: | Method 2: |
|---|---|---|
| Starting Peak Width | 50 | 8.0 |
| Peak Threshold | 0.5 | 25 |
| Peak Area Reject | 500 | 1000 |
| PED Recorder Range | 0.100 uC | 0.300 uC |

| Method 1: | | | | Method 2: | | | |
|---|---|---|---|---|---|---|---|
| Waveform: | | Integration: | | Waveform: | | Integration: | |
| Time (Sec) | Potential (V) | Begin (Sec) | End (Sec) | Time (Sec) | Potential (V) | Begin (Sec) | End (Sec) |
| 0.00 | 0.40 | 0.30 | 0.50 | 0.00 | 0.00 | 0.20 | 0.40 |
| 0.50 | 0.40 | | | 0.40 | 0.05 | | |
| 0.51 | 0.90 | | | 0.41 | 0.75 | | |
| 0.59 | 0.90 | | | 0.60 | 0.75 | | |
| 0.60 | −0.30 | | | 0.61 | −0.15 | | |
| 0.65 | −0.30 | | | 1.00 | −0.15 | | |

C. Fluophore Assisted Carbohydrate Electrophoresis (FACE)

Samples and standards were prepared for FACE using reagent kit (Glyko) and directions supplied by manufacturer. Suggested electrophoresis conditions were followed. Gels were imaged using a FACE Imager (Glyko).

Figure 2:
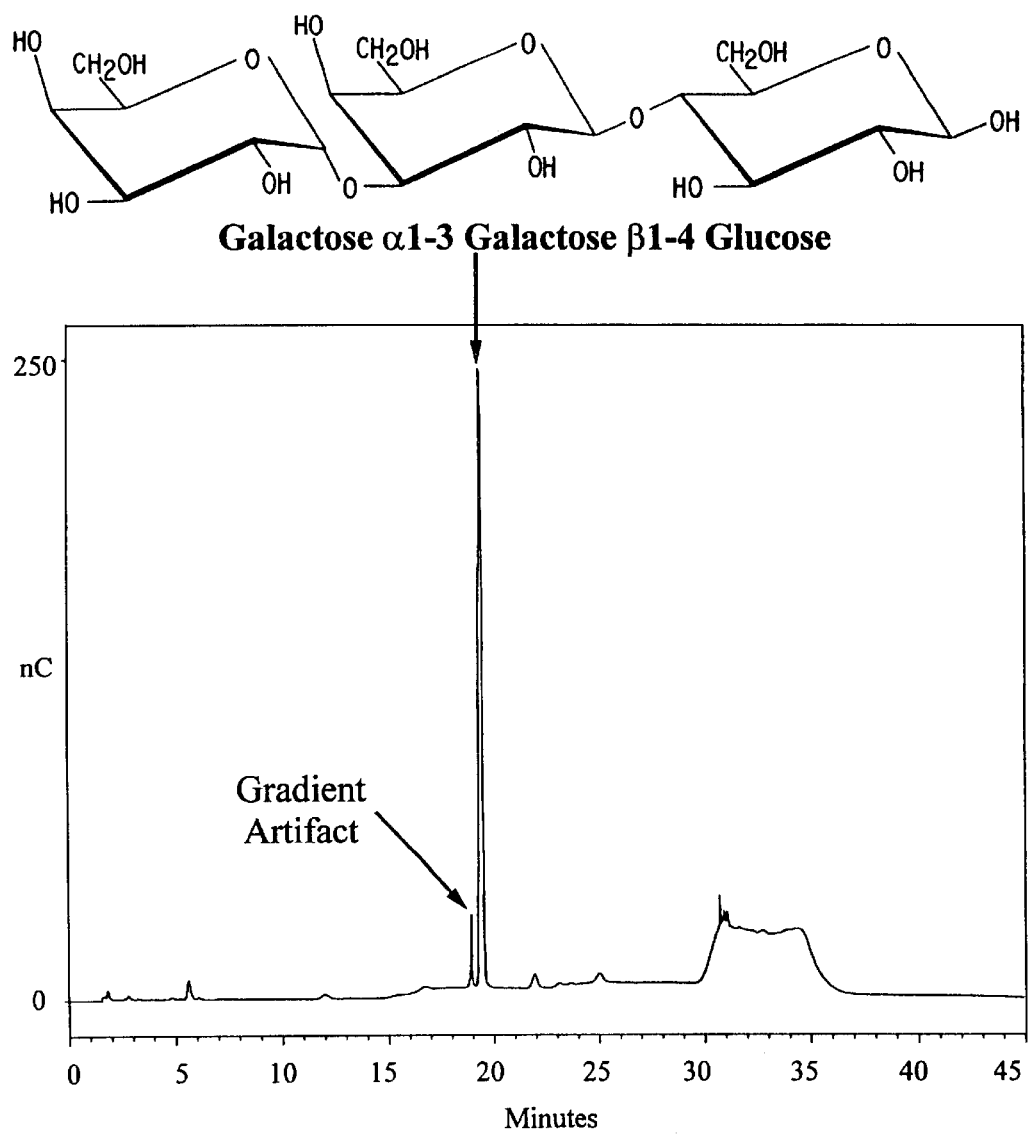
Figure 3:
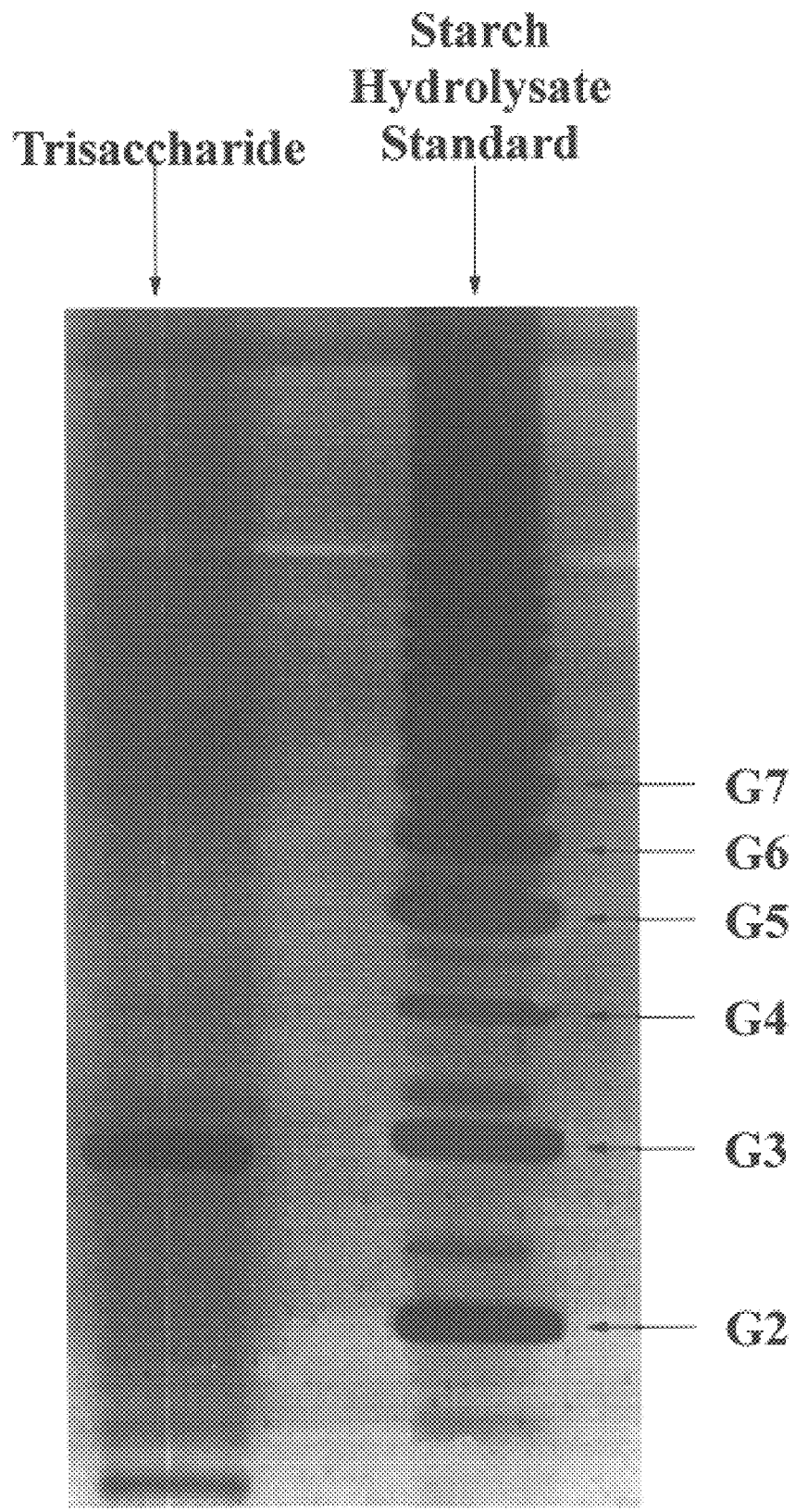

A standard of synthetic Gal$\alpha$1-3Gal $\beta$1-4Glc, 15 mMole (7.5 $\mu$g), was resuspended in 37.5 $\mu$l water to make a 200 ppm solution. 4 $\mu$l of this solution were diluted with 36 $\mu$l of water and analyzed by HPAEC (see FIG. 2 using Method 1). (The remaining stock standard was separated into 5 $\mu$l aliquots and stored frozen for future analyses.) Fractions (0.5 ml) were collected, and the fractions corresponding to standard peak (38–44) were pooled and dried overnight in Speed Vac at room temperature. The resulting dried pool was labeled for 3 hours at 45° C. per manufacturer's instructions and dried. The sample was then resuspended in 14 $\mu$l of water, and 2 $\mu$l (105 pmol) were diluted in 2 $\mu$l of loading buffer and loaded onto a polyacrylaminde gel. The gel was electrophorested per manufacturer's instructions. A fluorographic image of the gel is shown in FIG. 3.

Figure 5A:
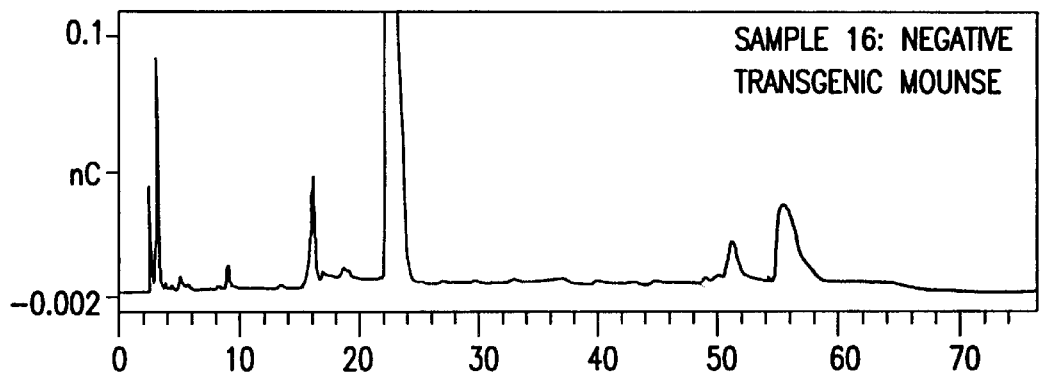
Figure 5B:
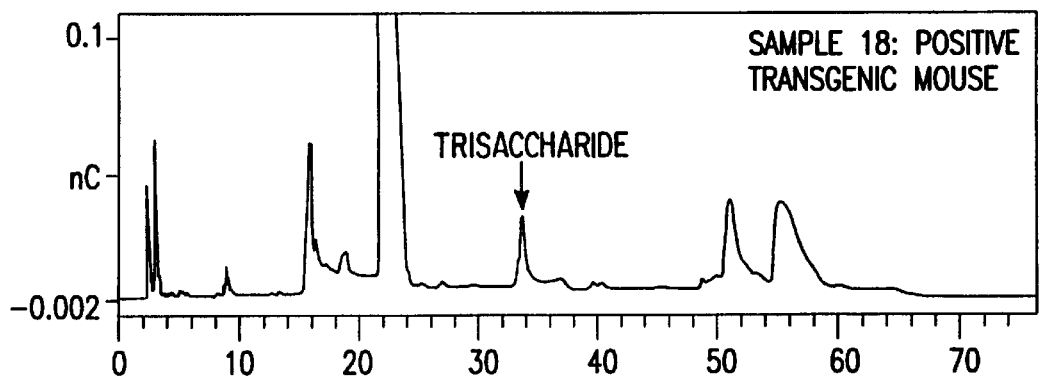
Figure 5C:
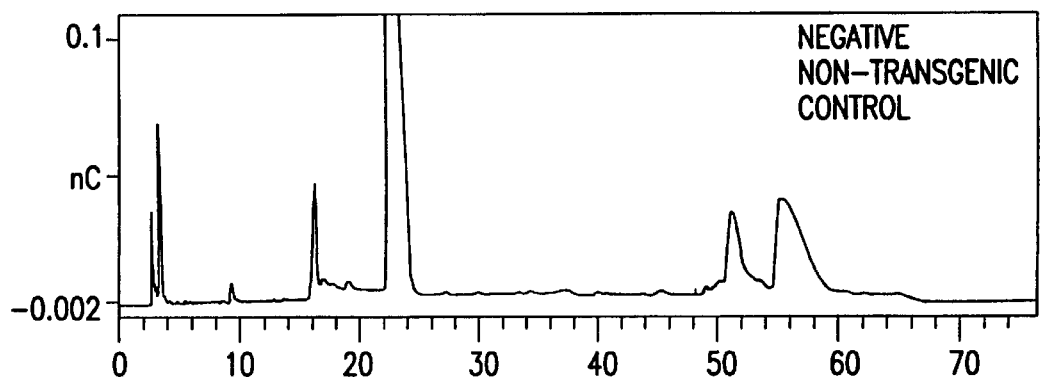
Figure 6:
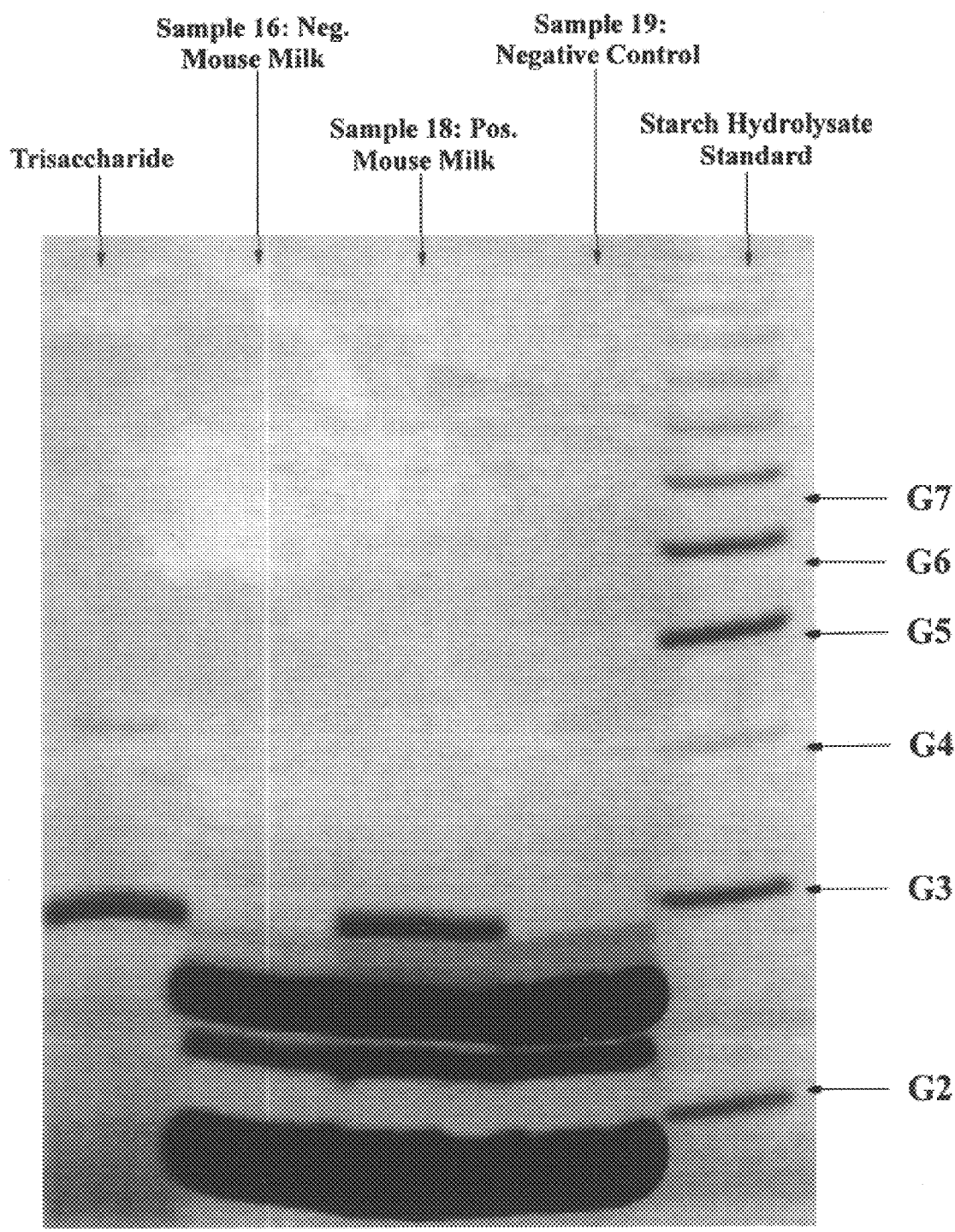

As noted in the Brief Description of the Drawings section, FIG. 5 shows an example of a negative transgenic, positive transgenic, and negative control mouse milk oligosaccharide profile as analyze using HPAEC Method 2. The large peak eluting at 31–32 minutes is presumed to be the trisaccharide. HPAEC Method 1 generated a small artifact peak that eluted very close to the trisaccharide standard and remained to run using Method 2, so to verify that the "new" peak detected was indeed the trisaccharide, the oligosaccharide extracts from these samples were labeled and tested by FACE. 8 $\mu$l of the oligosaccharide extracts were dried and labeled according to kit instructions. The labeled samples were resuspended in 10 $\mu$l of water, and 2 $\mu$l were loaded onto the gel. A previously labeled frozen sample of the trisaccharide standard was also run. The image of this gel is found in FIG. 6. The band that runs concurrent with the G3 starch by hydrolysate standard band is the trisaccharide.

D. Extraction of Mouse Milk

Mouse milk samples, which had been stored at −70° C., were thawed at room temperature. 100 $\mu$L were pipetted into a 500 $\mu$L Eppendorf centrifuge tube, and were centrifuged for 20 minutes at 11000 rpm using a BioFuge 15 (Baxter, McGaw Park, Ill.). The lipid pad was carefully removed, and the middle layer was transferred to a second 500 $\mu$L tube. A two-fold volume of cold (4° C.) ethanol was added, and the vial was vortexed and placed on ice for at least twenty minutes. The vial was then centrifuged as before. The clear supernatant was transferred to a third vial, and this extract was dried at medium heat overnight in a Speed Vac. The protein pellets were also dried, and were stored at −70° C. until analysis. The dried oligosaccharide extracts were resuspended in 100 $\mu$L water, and stored at −70° C. until analysis. Due to low quantity of available standard, it was not put through this entire procedure; however, other oligosaccharides have undergone this extraction method with no substantial losses in quantity (data not shown).

Table III displays a summary of all WAP/GT transgenic milk tested, sorted by the Founder numbers. Of the 23 "transgenic" samples tested (where "transgenic" is used to define a mouse that has tested positive for copies of the transgene in tail slot blots), 10 animals, or 44% of all animals in relevant germ lines, were positive for the synthesis of the trisachharide.

TABLE III

| 19 | B6SJL | | | | | | |
|---|---|---|---|---|---|---|---|
| 12 | B6SJL | | | | | | |
| 21 | B6SJL | | | | | | |
| 25 | B6SJL | | | | | | |
| 4 | 8 | 1 | 19 | hemi | 3061.187 | negative | 3 |
| 5 | 8 | 1 | 20 | hemi | 3061.187 | negative | |
| 3 | 8 | 1 | 22 | hemi | 3061.187 | negative | |
| 6 | 8 | 2 | 13 | homo | 3147.19 | negative | |
| 11 | 8 | 2 | 23 | homo | 3061.242 | negative | |
| 1 | 64 | 0 | | | 3061.11 | negative | ? |
| 13 | 82 | 1 | 71 | hemi | 3147.23 | negative | 1–2 |
| 7 | 98 | 0 | | | 3147.2 | negative | 1 |
| 16 | 106 | 1 | 93 | hemi | 3147.199 | negative | 1 |
| 29 | 106 | 2 | 61 | hemi | 3147.200 | negative | |
| 8 | 109 | 1 | 48 | hemi | 3147.21 | positive | 1–2 |
| 15 | 109 | 1 | 67 | hemi | 3147.24 | positive | |
| 20 | 109 | 1 | 118 | hemi | 3147.2 | negative | |
| 22 | 109 | 2 | 50 | hemi | 3147.2 | negative | |
| 27 | 109 | 2 | 51 | hemi | 3147.2 | positive | |
| 17 | 109 | 2 | 51 | hemi | 3147.2 | positive | |
| 18 | 109 | 2 | 53 | hemi | 3147.2 | positive | |
| 28 | 109 | 2 | 54 | hemi | 3147.2 | positive | |

TABLE III-continued

| 2  | 156 | 0 |     |      | 3061.187 | positive   |
|----|-----|---|-----|------|----------|------------|
| 9  | 156 | 0 |     |      | 3061.242 | positive   |
| 10 | 156 | 1 | 42  | hemi | 3061.242 | positive   |
| 23 | 156 | 1 | 100 | hemi | 3147.199 | negative   |
| 26 | 156 | 2 | 27  | hemi | 3147.200 | positive   |
| 14 | 193 | 0 |     |      |          | not tested |
| 24 | 193 | 1 | 120 | hemi |          | not tested |

(Note: the samples identified as "Founder B6SJL" were the negative control/non-transgenic mice.)

Note in Table III that milk samples from the same founder may or may not test positive for the synthesis of the trisaccharide; possession of a copy (or copies) of the transgene in the DNA does not guarantee that the mouse will be able to synthesize the trisaccharide. (For example, see results of milks from various animals related to Founder 109.) It may be possible that these samples contained the trisaccharide; however, it was produced below the detection limit of the method (approx. 10 ppm).

Figure 4:
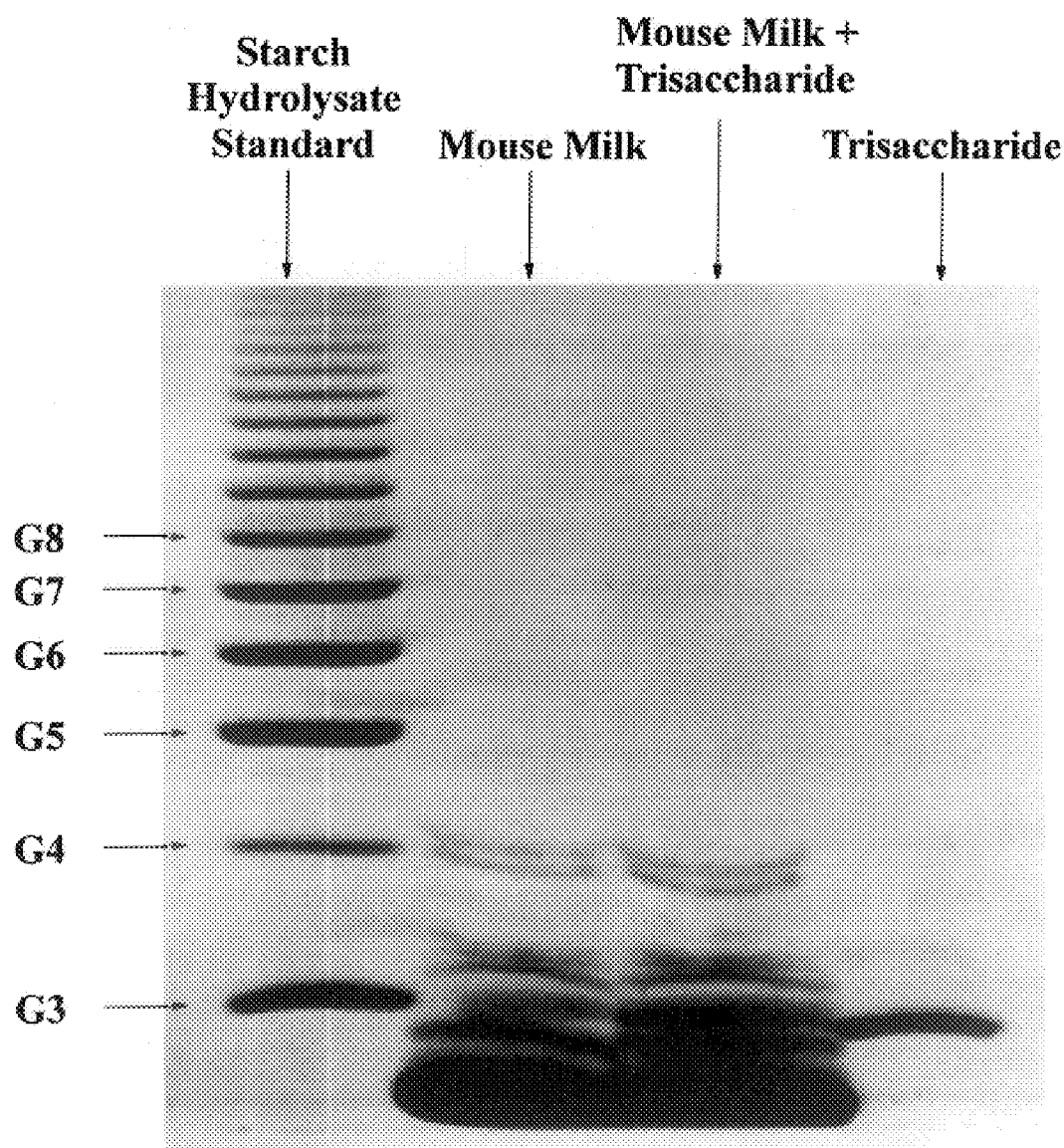

E. Spiking of Control Mouse Milk with Trisaccharide Standard 1852 pmol of trisaccharide standard were dried in a 500 μl eppendorf centrifuge tube. 100 μl control (non-transgenic) mouse mile was added, and the vial contents were mixed well. This spiked milk sample was then defatted and deproteinated as described above. 45 μl ethanol extract was recovered, of which 20 μl (containing a theoretical 820 pmol of trisaccharide) were dried and labeled 3 hours at 45° C. for oligosaccharide analysis (Glyko). After drying, the sample was resuspended in 10 μl water, and 2 μl were loaded onto a FACE gel. The image is found in FIG. 4. An unspiked control milk sample was also analyzed for comparison.

All samples and/or standards in C and D were analyzed using HPAEC as prepared, without further dilution.

EXAMPLE II

Expression of Human α1,2-Fucosyltransferase in Rabbits (Heterologous Expression)

Creation of transgenic embryos was carried out in collaboration with Dr. John Kopchick and his colleagues at the Edison Biotechnology Institute at Ohio University in Athens, Ohio, and with Zdizislaw Smorage at the Zootechnics Institute in Balice, Poland. 90% of the rabbits used were New Zealand bred, with the remaining 10% being California bred.

A. Preparation of Transgenic Zygotes

Zygotes were collected from superovulated female rabbits which were 4–6 months old. Superovulation was achieved by standard procedures employing 50–i.u. of Pregnant Mare Serum Gonadotropin (PMSG) injected intramuscularly, followed by 50–100 i.u. of Human Chorionic Gonadotropin (HCG) injected intravenously 72 hours after PMSG. Immediately after HCG injection, superovulated females were mated or inseminated with fresh or frozen semen from 5 month old males. 20–22 hours after insemination or mating, females were slaughtered, and zygotes were collected by oviduct flushing supplemented with PBS. Zygotes were microinjected with DNA (i.e., a linear DNA fragment excised from a previously described plasmid (Prieto et al., Journal of Biological Chemistry 270:29515–29519 (1995)) containing a transcriptional regulatory region which included the murine whey acidic protein promoter, a cDNA encoding the human H-α1-2 fucosyltransferase and a sequence encoding the polyadenylation signal of bovine growth hormone) encoding 2'-fucosyltransferase at 2–6 ng/ml, 1–2 hours after flushing, using an inverted microscope with Namarski optics, and micropipets connected with Da Venbrine or Leitz micromanipulators.

B. Implantation of Transgenic Zygotes & Collection of Milk

One hour after microinjection, the zygotes were surgically transferred into oviducts of synchronized, pseudopregnant recipients who were 5–6 months old. The progress report of the insemination project is given in Table IV. The resulting pups were analyzed for successful transcription of the DNA by dot blot analyses. Milk from two of these animals, along with that from non-transgenic controls, was collected and analyzed.

TABLE IV

Insemination Progress Report

| Group Number | No. of Inseminated Females | No. of Pregnant Females | No. of Rabbits Born Alive | No. of Stillborn Rabbits |
|---|---|---|---|---|
| I   | 8  | 7  | 26  | 1  |
| II  | 4  | 4  | 16  | 8  |
| III | 20 | 16 | 67  | 17 |
| IV  | 20 | 7  | **  | ** |
| Total | 52 | 34 | 109 | 26 |

(**Information not available at this time)

C. Preparation of Milk Obtained From Pups

Milk samples from transgenic and control rabbits were diluted 1:3 with ethanol and shipped to Ross Laboratories (Columbus, Ohio). They were vortexed well and centrifuged 10 minutes at 10,000 rpm. The ethanol layer was removed and placed in a clean vial for oligosaccharide analysis, and the precipitates were frozen for future protein analysis.

D. Oligosaccharide Profiling

Fifty μl of each of the ethanol extracts were diluted with 50 μl water. The dilutions were filtered through pre-rinsed 30,000 MWCO filters (Microcon, Amicon, Inc., Berverly, Mass.), and were analyzed using HPAEC Method 1 (see Appendix I at end of this example). Spiked samples of one of each control and transgenic samples were prepared by diluting a 50 μl sample with 48 μl water and 2 μl 1000 ppm 2'-fucosyllactose, and filtering as before. These samples were also analyzed. A second set of milk samples was analyzed as received, with no further dilution.

Of the remaining ethanol extracts, 240 μl were dried in a Speed Vac (Savant, Inc., Farmingdale, Ill.). The extracts were then resuspended to volume with 7% IPA and filtered through Microcon 30,000 MWCO as before. 20 μl of each sample from set one, and 50 μl from each sample of set two, were dried and labeled overnight according to manufacture's instructions (Glyko, Inc., Novato, Calif.). They were then labeled overnight according to manufacturer's instruction (Glyko, Inc.). The labeled samples were resuspended in 10 μl water. 2 μl of each were loaded onto an oligosaccharide gel and electrophoresed.

E. Fucosidase Treatment

25 μl of the filtered IPA dilutions from set one were dried in 2 separate vials, along with two 2'-fucosyllactose (2'-FL) aliquots of 1000 ppm. The samples were resuspended in 25 μL 1× PBS, pH 8.5. 200 mU α1,2-fucosidase from Arthrobacter oxidans (Takara-Panvera, Madison, Wis.) in PBS were added to each one of the vials. The same volume of a boiled (deactivated) enzyme was added to the second vial.

The samples were incubated at 37° C. overnight under a toluene atmosphere. They were filtered through rinsed Centricon 10,000 MWCO filters (Amicon), using 950 µl water to rinse. The filtrates were then passed through On-Guard A—strong anion-exchange cartridges (Dionex), which were prepared according to manufacturer's instructions. The samples were rinsed through with 200 µL water. The collected filtrates were frozen, dried, and labeled overnight for FACE analysis (Glyko). The samples were diluted in 10 µl water, and a 2 µl aliquot of this material was subjected to electrophoresis and imaging.

F. SDS-PAGE and Western Blots of Glycoproteins

The proteins pellets were thawed to room temperature, washed twice with cold 68% ethanol, and dried. They were resuspended in 2× SDS denaturing buffer. The samples were heated in boiling water for 5 minutes to denature the proteins and were cooled. Dilutions were made using 1× SDS buffer. Samples and Prestained Low Molecular Weight Standard (Sigma, St. Louis, Mo.) were loaded onto a polyacrylamide gel (Novex, Inc., San Diego, Calif.) and electrophoresed in the Xcell II Mini Cell System (also from Novex). The gel thus obtained was transferred to a PVDF membrane, and probed with Ulex europaeus Agglutinin I (UEA I)(peroxidase labeled, Sigma) overnight. After washing with TBS-Tween 20, the gel was developed using a DAB-Hydrogen Peroxide Staining solution (Sigma). The dried gel was scanned and digitized using an ordinary 300 dpi computer scanner.

Figure 7C:
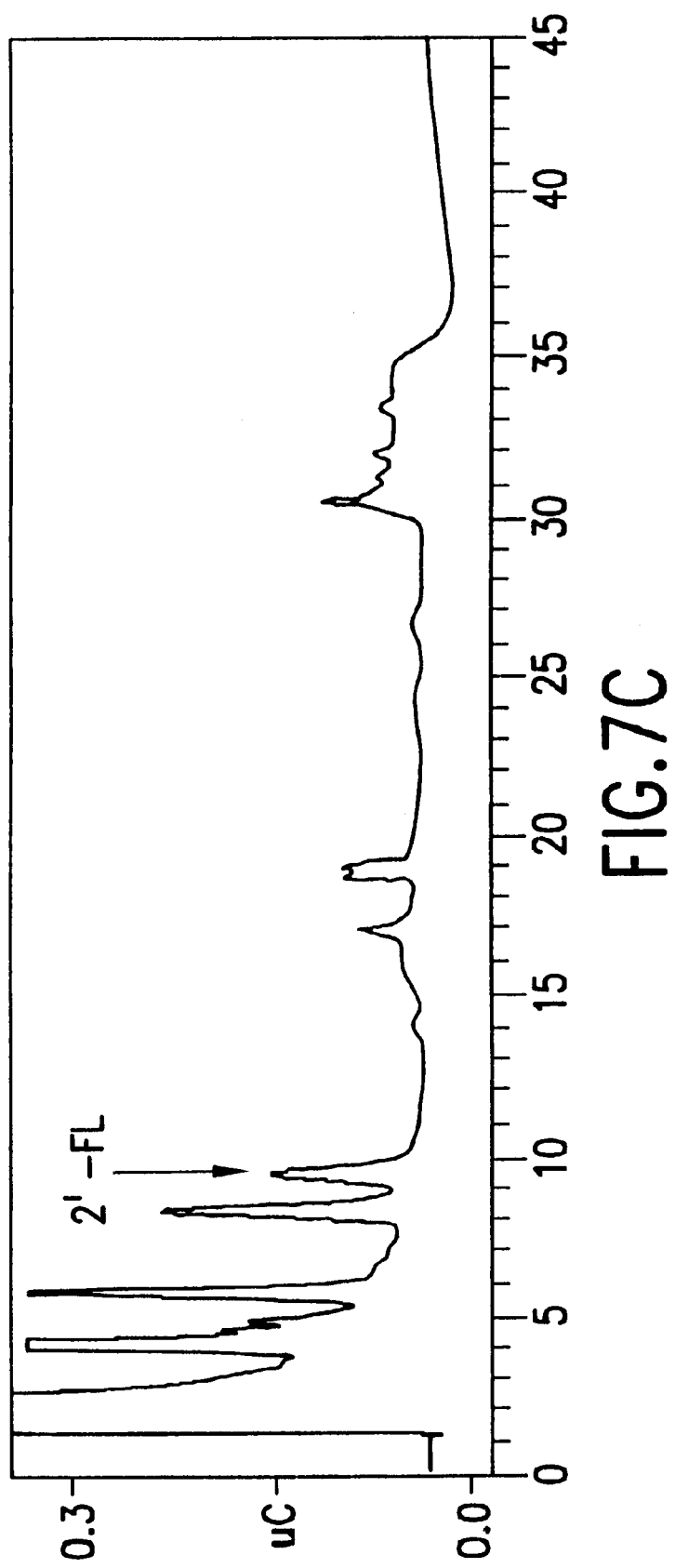
FIGS. 7–13 relate to a method involving expression of a heterologous enzyme (i.e., H-α-1,2-fucosyltransferase).
Figure 8A:
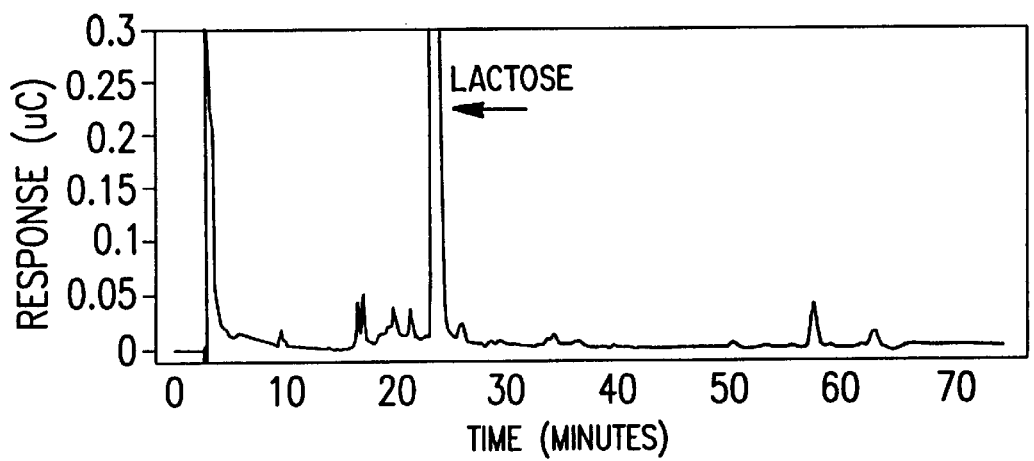
Figure 8B:
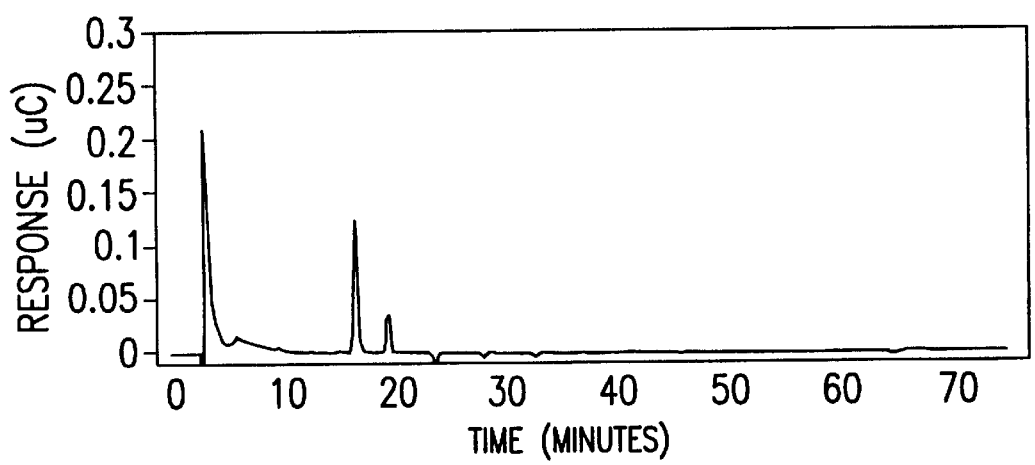
Figure 8C:
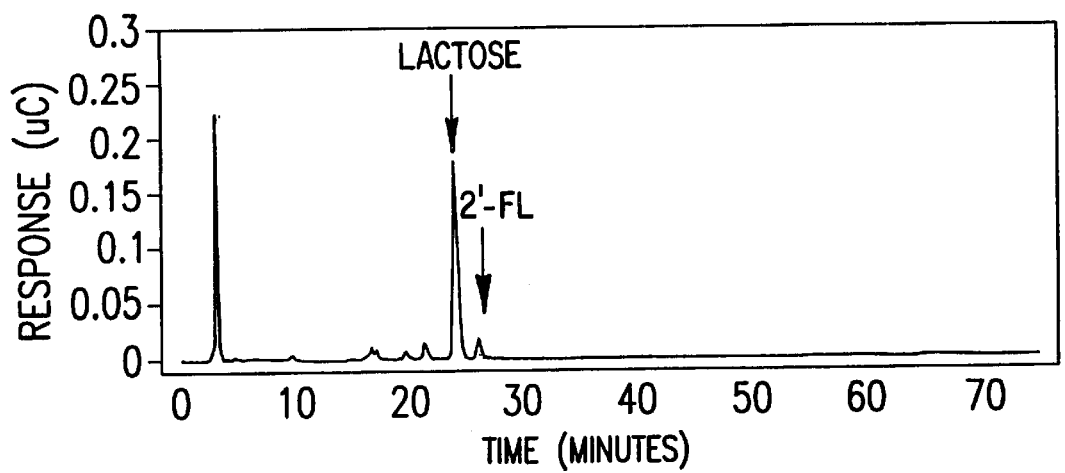
Figure 8D:
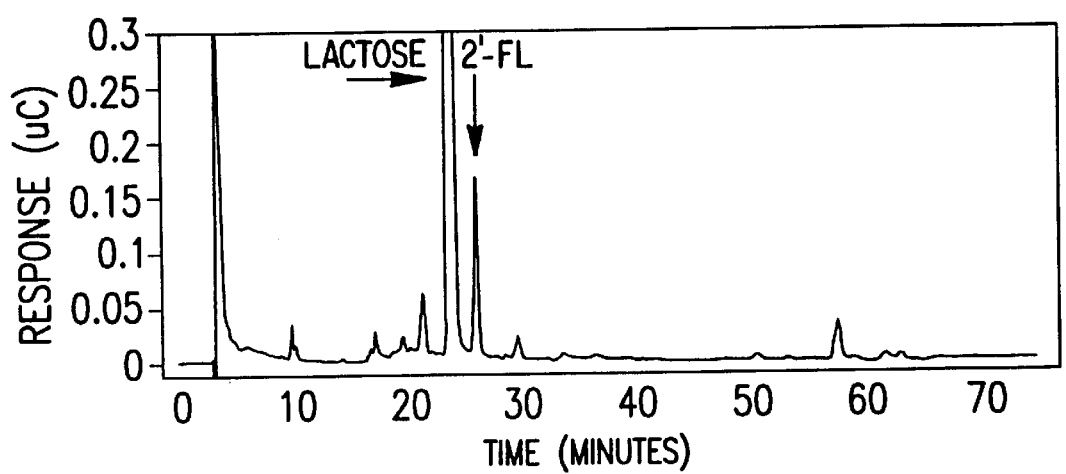

The results were as follows:

FIG. 7 contains the chromatographic oligosaccharide profiles of control non-transgenic, positive transgenic, and spiked-positive transgenic rabbit milk samples as obtained from one sample. Transgenic sample #1 contained 2'-FL, a fact corroborated by the spiked profile. Note the large difference in lactose concentration between the control and the transgenic sample. A second transgenic sample (#2), which was found to be negative (containing no 2'-FL), is not shown. Of the profiles found in FIG. 8, samples #4 (panel C) and #5 (panel D) contained 2'-FL in quantities detectable by this method. This sample exhibited a marked decrease in lactose concentration while sample #3 (panel B) had no detectable amounts of lactose.

Figure 9:
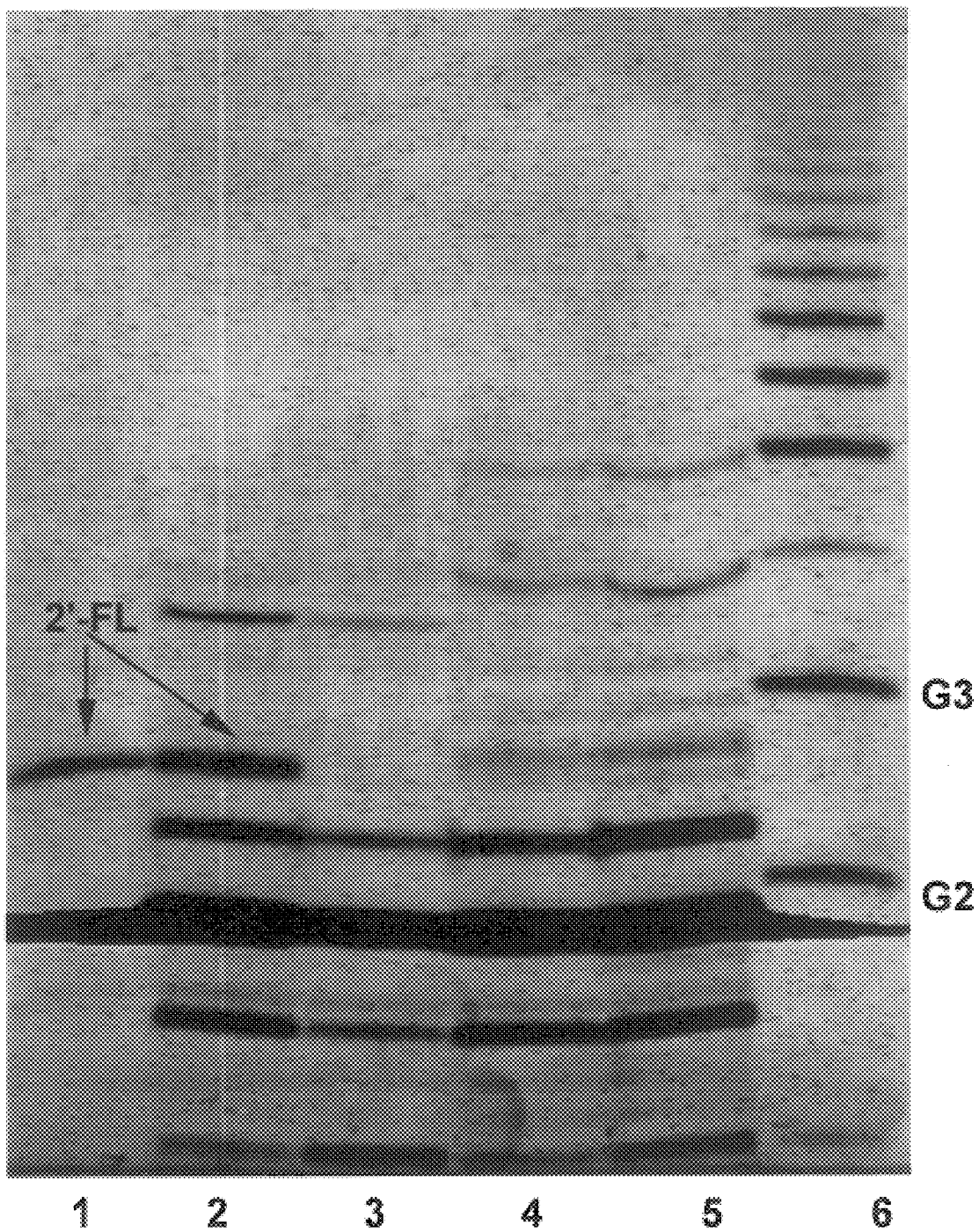

To further verify the nature of the oligosaccharide present in milk samples from transgenic animals, oligosaccharides from control non-transgenic and transgenic milk were subjected to hydrolysis by α1-2 fucosidase. This enzyme exclusively hydrolyzes fucose 1–2 linkages. Results are shown in FIG. 9. Authentic 2'-fucosyllactose (2'-FL) is shown in Lane 1 while untreated oligosaccharides from a transgenic sample are shown in Lane 2. Lane 3 shows the same material as in Lane 2, but after fucosidase treatment. A band comigrating with authentic 2'-FL is clearly observable in Lane 2. This band disappeared after fucosidase treatment, further supporting the presence of 2'-FL in the transgenic milk sample. Oligosaccharides from a control non-transgenic sample were substantially unchanged after fucosidase treatment (see Lanes 4 and 5).

Figure 10:
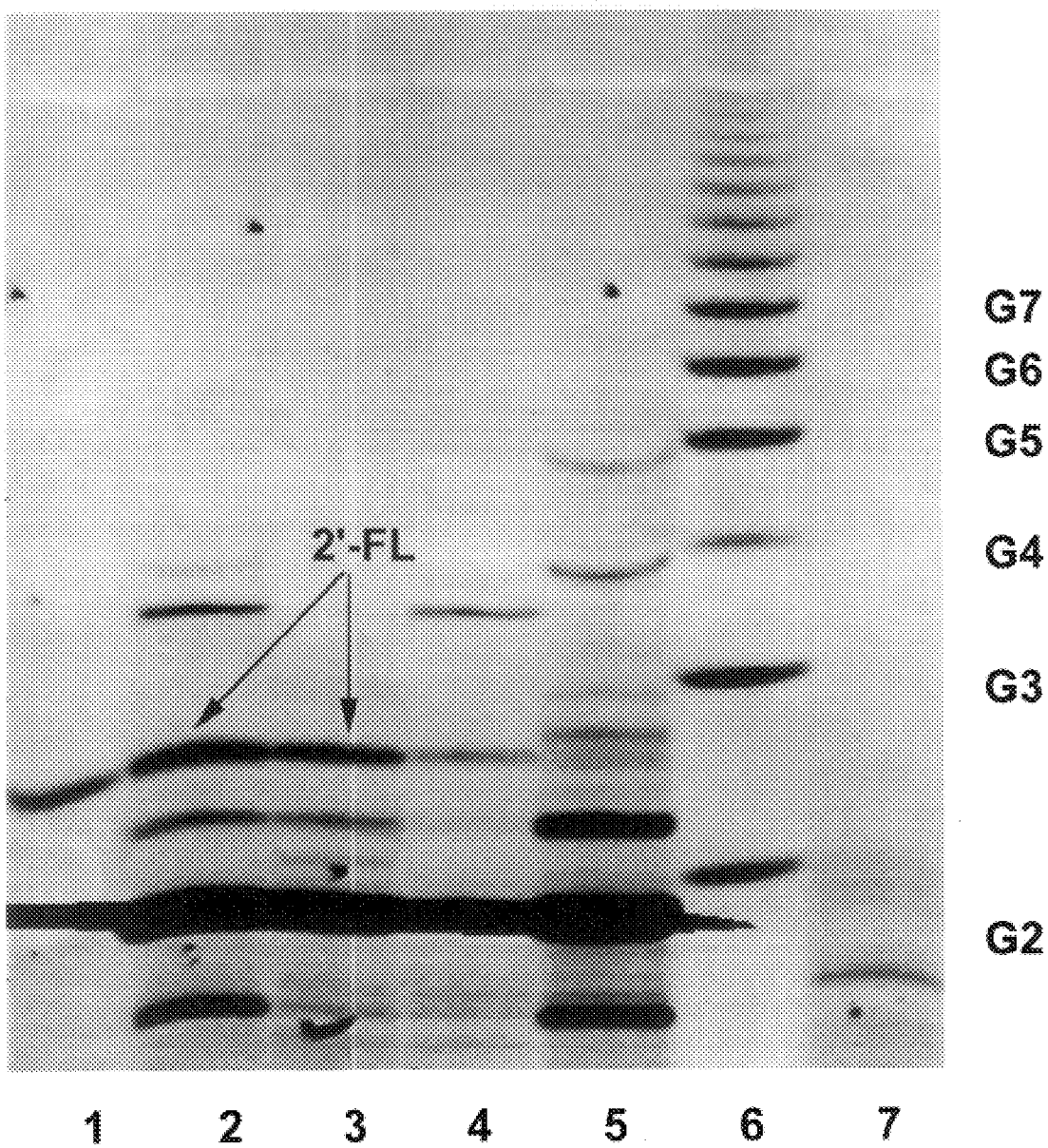

FACE oligosaccharide profiles of additional milk samples are shown in FIG. 10. Lane 2 of this figure shows the resolved labeled oligosaccharides from milk of sample #5. Lane 3 shows the oligosaccharides of another transgenic milk sample. Lane 4 shows the oligosaccharides of sample #4. Lane 5 is the profile from a control non-transgenic animal, and Lane 7 is sample #3. These results corroborate the chromatographic profiles of FIG. 8 and further support the concept that some transgenic milk samples were devoid of lactose.

Figure 11:
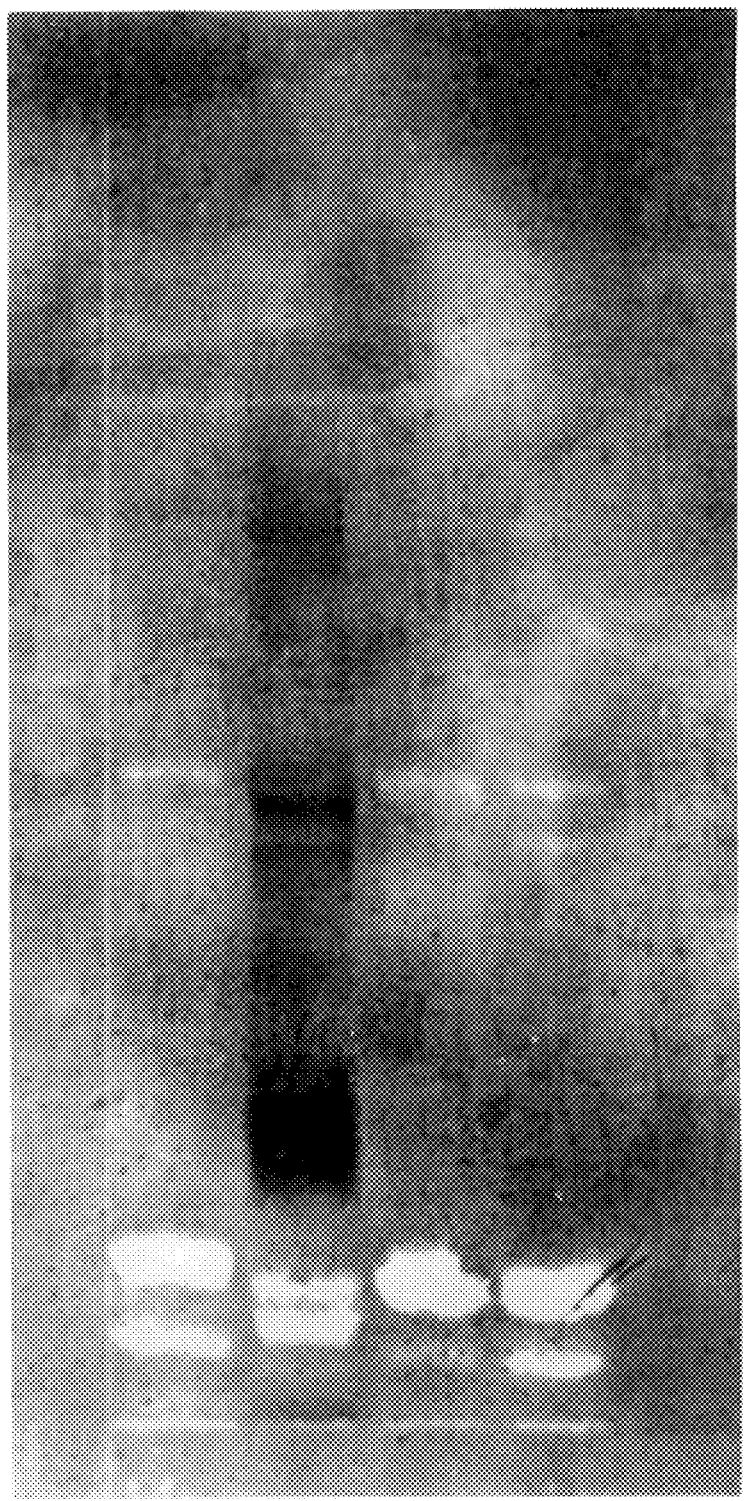
Figure 12:
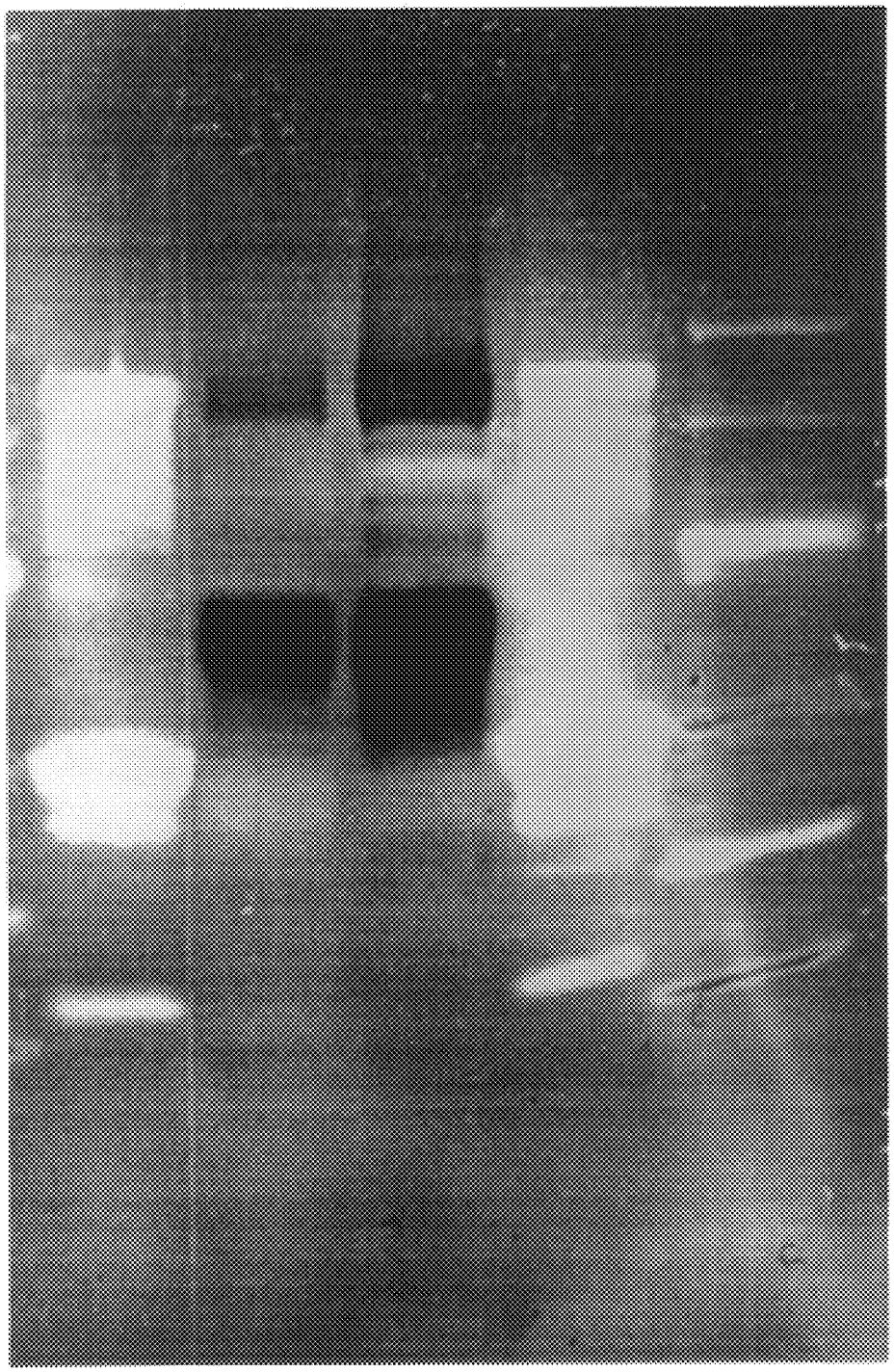
Figure 13:
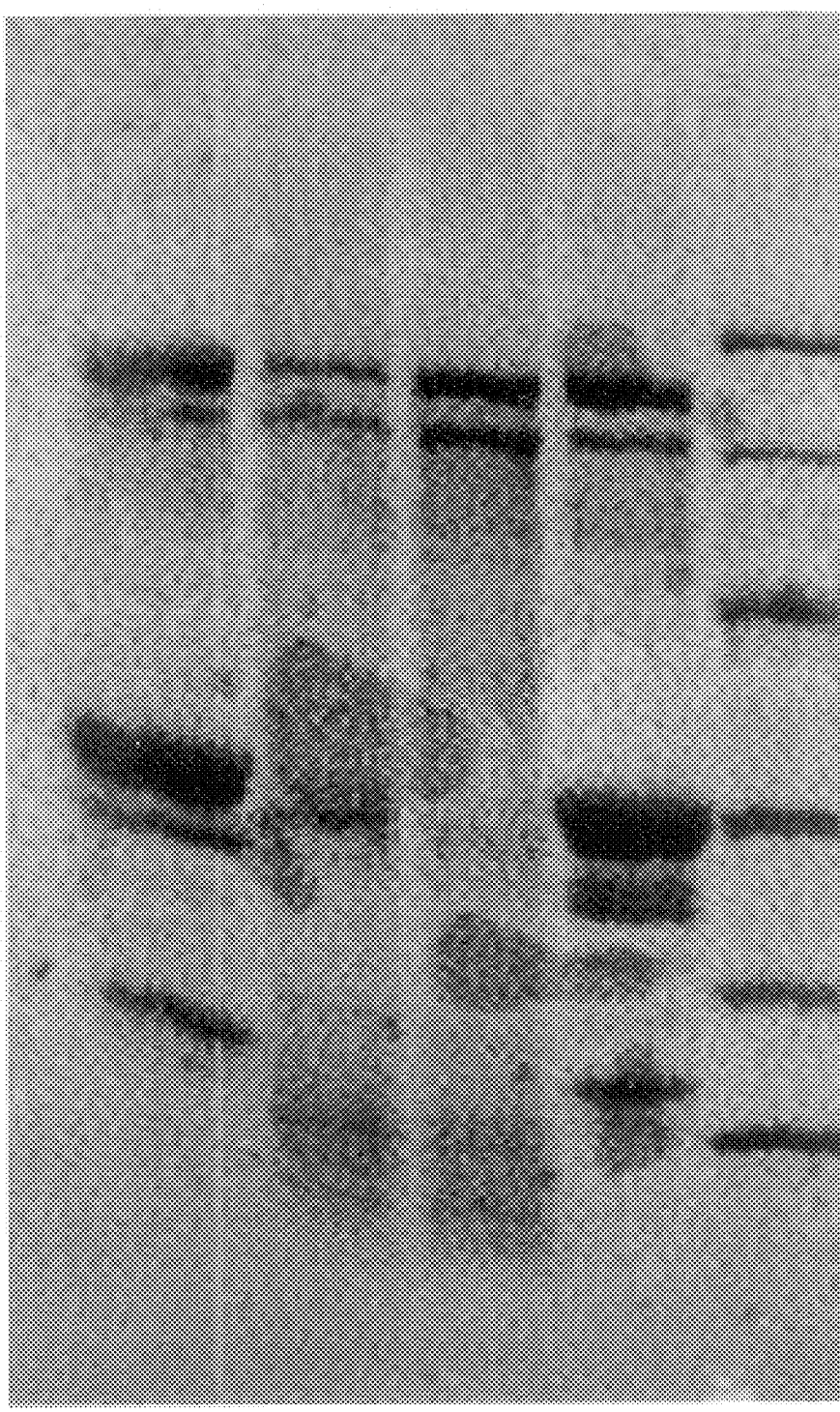

FIG. 11 compares Western blots of milk protein samples #1 and #2, probed with UEA-I. Positive bands are seen only in Lane 2, one of the positive transgenic samples. Neither sample #2 nor the non-transgenic control, contained proteins which are glycosylated with fucose in the α-1,2 linkage. Western blots for additional samples are shown in FIG. 12. As expected, sample #4 contained proteins which are fucosylated in the alpha-1,2 position. Sample #3, however, also contained similarly decorated proteins. This result was not expected due to the lack of detectable 2'-FL which the other two methods missed. All other samples analyzed to date (including those from mice) have contained, at least, fucosylated proteins. The Coomassie stain of a gel identical to that found in FIG. 12 is presented as FIG. 13. This figure illustrates that, although no proteins were detected by UEA-I in the non-transgenic controls, there were many proteins present in the sample. As a contrast, compare the total proteins found in samples #3 and #4 to the bands detected in the UEA-I blot. Although they were present in almost non-detectable quantities, they were strongly detected by the lectin.

---

Appendix I: Chromatography Conditions

Oligosaccharide Analysis by High-Pressure Anion-Exchange Chromatography:
Samples were analyzed using a Dionex Bio-LC system, equipped with a Pulsed-electrochemical detector, employing a single analytical CarboPac PA-1 column with guard. Conditions were as follows:

Sensitivity: 0.200C
Run Time: 45 minutes
Peak Width: 8.0 seconds
Peak Threshold: 25.00
Peak Area Reject: 1000
Sample Volume: 20L Gradient Program:

| | |
|---|---|
| 0–12 minutes: | 100 mM NaOH |
| 12.1–20 minutes: | 42 mM NaOAc in 100 mM NaOH |
| 20.1–27 minutes: | 60 mM NaOAc in 100 mM NaOH |
| 27.1–32 minutes: | 300 mM NaOAc in 100 mM NaOH |
| 32.1–45 minutes: | 100 mM NaOH |

PED Program:

| Waveform: | | Integration: | |
|---|---|---|---|
| Time (sec): | Potential (V): | Begin (sec): | End (sec): |
| 0.00 | 0.05 | 0.20 | 0.40 |
| 0.40 | 0.05 | | |
| 0.41 | 0.75 | | |
| 0.60 | 0.75 | | |
| 0.61 | −0.15 | | |
| 1.00 | −0.15 | | |

EXAMPLE III

Expression of Human Fucosyltransferase IV in Mice (Heterologous Expression)

A human fucosyltransferase (i.e., the "H" fucose α1-2-transferase) has previously been expressed in lactating mammary glands of mice (Prieto et al., *Journal of Biological Chemistry*, 270:29515–19 (1995)). Its expression resulted in the production of oligosaccharides and glycoproteins synthesized by the enzyme. In order to demonstrate the potential, broad application of this system for the production of secondary gene products, the present inventors decided to transgenically express a glycosyltransferase, other than the human H-fucose α1-2-transferase, in mice. One such enzyme is fucosyltransferase IV (Kukosawa-Latallo et al., *Genes and Development* 4:1288–1303 (1989)). This enzyme is present in certain samples of human milk (Serenella et al., *Glycoconjugate Journal* 6:101–114 (1989)) and is of particular interest because it is responsible for the synthesis of certain blood group antigens (Legault et al., The *Journal of Biological Chemistry* 270:20987–20996 and Ginsburg et al., in *Immunology of the Erythrocyte,* Alan R. Liss, Inc., New York, N.Y.). These blood group antigens are important because they are elevated during presence of cancer (Orntof et al., *The Journal of Biological Chemistry* 271:32260–32268 (1996)) and have been implicated in cell adhesion phenomenae such as inflammation (Lowe et al., *The Journal of Biological Chemistry* 266:17467–17477)). The expression of the human enzyme fucosyltransferase IV and synthesis of 3-fucosyllactose were carried out as described below:

The following reagents were utilized:

500 mM sodium hydroxide and 200 mM sodium hydroxide, RICCA Chemical Company (Arlington, Tex.), carbonate free NIST-traceable (Baxter Inc., McGaw Park, Ill.)

sodium acetate, ACS grade, (Sigma, St. Louis, Mo.)

FACE Reagent Kit (Glyko Inc., Novato, Calif.)

Milli-Q Water (Millipore, Bedford, Mass.)

Sulfuric Acid Ultrex Ultrapure Grade (Baxter)

Sample Drying: All samples and standards were dried using a Speed Vac Plus SC210A equipped with a Refrigerated Vapor Trap RVT4104 (Savant, Farmingdale, Ill.).

A. Preparation of Plasmid and Creation of Transgenic Embryos

The genetic construct was prepared at the Edison Biotechnology Institute at Ohio University (Athens, Ohio). A cDNA (i.e., a linear DNA fragment excised from a previous described plasmid (Prieto et al., *Journal of Biological Chemistry* 270:29515–29519 (1995)) containing a transcriptional regulatory region which included the whey acidic protein promoter, a cDNA encoding the human α1-3/4- fucosyltransferase (FucT-IV) and a sequence encoding the polyadenylation signal of bovine growth hormone) encoding the human fucosyltransferase (IV) was inserted into a plasmid containing the polyadenylation signal of bovine growth hormone (bGH polyA) and the lactogenically-responsive murine whey acidic protein (WAP) promoter. An EcoRI-BamHI fragment was microinjected into the pronuclei of mouse embryos. The presence of the gene was detected by tail slot blots. Milk from lactating females was collected and stored frozen at −70° C. until shipped to Ross Laboratories (Columbus, Ohio) for carbohydrate analysis. Three transgenic females were obtained. Milk from two of these females was collected and analyzed.

B. HPAEC Analysis of Samples and Standards

Mouse milk oligosaccharides and oligosaccharide standards were analyzed using a Dionex Bio-LC System, equipped with the following:

Pump: Dionex Advanced Gradient Pump

Detector: Dionex Pulsed Electrochemical Detector with gold working electrode and pH/reference electrode Autosampler: Spectrophysics Refrigerated AS3500

Columns: 2 Dionex CarboPac PA1 analytical columns (4×250 mm each, connected in serial) preceded by a guard (4×50 mm)

Chemical Supression: Dionex AMMS-II Anion Micromembrane Suppression, (installed after detector but before fraction collector, used to neutralize samples), regenerated by 0.15% sulfuric acid using Dionex AutoRegen Apparatus and Anion Regenerant Cartridge Fraction Collector: BioRad Model 2110 (BioRad Inc., Hercules, Calif.)

All equipment was purchased from Dionex, Inc. (Sunnyvale, Calif.) unless otherwise noted. Eluants used were a combination of (A) Milli-Q water (or equivalent), (B) 500 mM sodium hydroxide, (C) 600 mM sodium acetate in 100 mM sodium hydroxide, and/or (D) 200 mM sodium hydroxide, at a flow rate of 1.0 ml/min. Table V below contains the eluant profiles for the two methods used. Detector settings are as listed in Table VI below. Injection volume was 20 µL.

All samples and/or standards were analyzed as prepared without further dilution. When further characterizations was deemed necessary. Fractions were collected (0.5 minutes per fraction) and dried in their collection tubes. These samples were then labeled for FACE analysis. Whenever possible, chromatograms were obtained for transgenic and control animals. As preliminary characterization step, aliquots were spiked with authentic standards of 3-fucosyllactose. In this fashion, coelution of neooligosaccharide with authentic 3-fucosyllactose was demonstrated.

TABLE V

Eluant Profiles

Method

| Time (min) | 0/0 A | 0/0 B | 0/0 C | 0/0 D |
|---|---|---|---|---|
| 0.0 | 99 | 1 | 0 | 0 |
| 60.0 | 0 | 10 | 0 | 0 |
| 60.1 | 99 | 1 | 0 | 0 |
| 75.0 | 99 | 1 | 0 | 0 |

A = Milli-Q Water
B = 500 mM NaOH
C = 600 mM NaOHAc/100 mM NaOH
D = 200 mM NaOH

TABLE VI

Detector Settings

| Integration Parameters: | Method 1: | Method 2: |
|---|---|---|
| Starting Peak Width | 50 | 8.0 |
| Peak Threshold | 0.5 | 25 |
| Peak Area Reject | 500 | 1000 |
| PED Recorder Range | 0.100uC | 0.300uC |

Method

| | Waveform: | | |
|---|---|---|---|
| | Potential | Integration: | |
| Time (sec) | (v) | Begin (sec) | End (sec) |
| 0.00 | 0.00 | 0.20 | 0.40 |
| 0.40 | 0.05 | | |
| 0.41 | 0.75 | | |
| 0.60 | 0.75 | | |
| 0.61 | −0.15 | | |
| 1.00 | −0.15 | | |

C. Fluorophore Assisted Carbohydrate Electrophoresis (FACE)

Samples and standards were prepared for FACE using a reagent kit and directions supplied by manufacturer (Glyko, Novalto, Calif.). Suggested electrophoresis conditions were followed. Gels were imaged using a FACE Imager (Glyko).

Samples of milk oligosaccharide extracts (10 µl) were dried and labeled 3 hours at 45° C. for oligosaccharide analysis (Glyko) as previously described. After drying, the sample was resuspended in 10 µl of water, and 2 µl were loaded onto a polyacrylamide oligosaccharide resolving gel. Images of the electrophoretograms were obtained using a Glyko Face Imager.

D. Extraction of Mouse Milk

Mouse milk samples which had been stored at −70° C., were thawed at room temperature and mixed by vortexing. 50 µl were pipetted into a 500 µl Eppendorf and 100 µl of cold absolute ethanol were added The resulting mixture was vortexed and centrifuged for 15 minutes at 4° C. and 11000 rpm using a BioFuge 15 (Baxter, McGaw Park, Ill.). After centrifugation, 85 µl of clear supernatant were transferred into another 500 µl centrifuge tube, and 199 µl of distilled deionized water were added. The resulting mixture was mixed well, and 50 µl were transferred to an autosampler vial, diluted 1:1 with water and submitted to High pH Anion Exchange Chromatography (HPAEC). This final solution was considered the oligosaccharide extract of the milk sample.

E. Spiking of Milk with Authentic 3-Fucosyllactose

A solution of 3-fucosyllactose Galβ1-4[Fucα1-3]Glc of 50 mg/liter was added to 50 µl of the oligosaccharide extract described above and mixed well. This spiked milk sample was then directly submitted to chromatography and compared with an oligosaccharide extract that was diluted with a volume of water.

F. Exoglycosidase Treatments

Fucosidases from *Corynebacterium sp.* (α1-2 specific) and *Streptomyces sp.* (α1-3/4 specific) were from Takara Panvera, (Madison, Wis.). *E. coli* and other chemicals used were of the highest purity available and, unless otherwise indicated, were from Sigma Chemical Co. (St. Louis, Mo.).

G. Separation of Neutral and Charged Oligosaccharides

Oligosaccharide extracts (200 µl aliquots) were separated into neutral and charged fractions to facilitate detection and identification of neooligosaccharides synthesized by the action of the transgene encoded fucosyltransferase.

A column (3 ml) of DE-52 (diethylaminoethyl cellulose, Whatman, Maidstone, England) was equilibrated in 0.002 M pyridine acetate buffer pH 5.4 by passing approximately 20 volumes of the buffer through it. The oligosaccharide extract aliquot was applied to the column, allowed to permeate into the resin and to rest for 5 to 10 minutes. The neutral oligosaccharides were then eluted by eluting the column with 6 volumes of the same buffer. The fraction thus obtained was dried and prepared for labeling and fluorophore assisted carbohydrate electrophoresis. The charged fraction was subsequently eluted from the column by rinsing it with five volumes of 0.2 M pyridine acetate buffer.

Figure 14B:
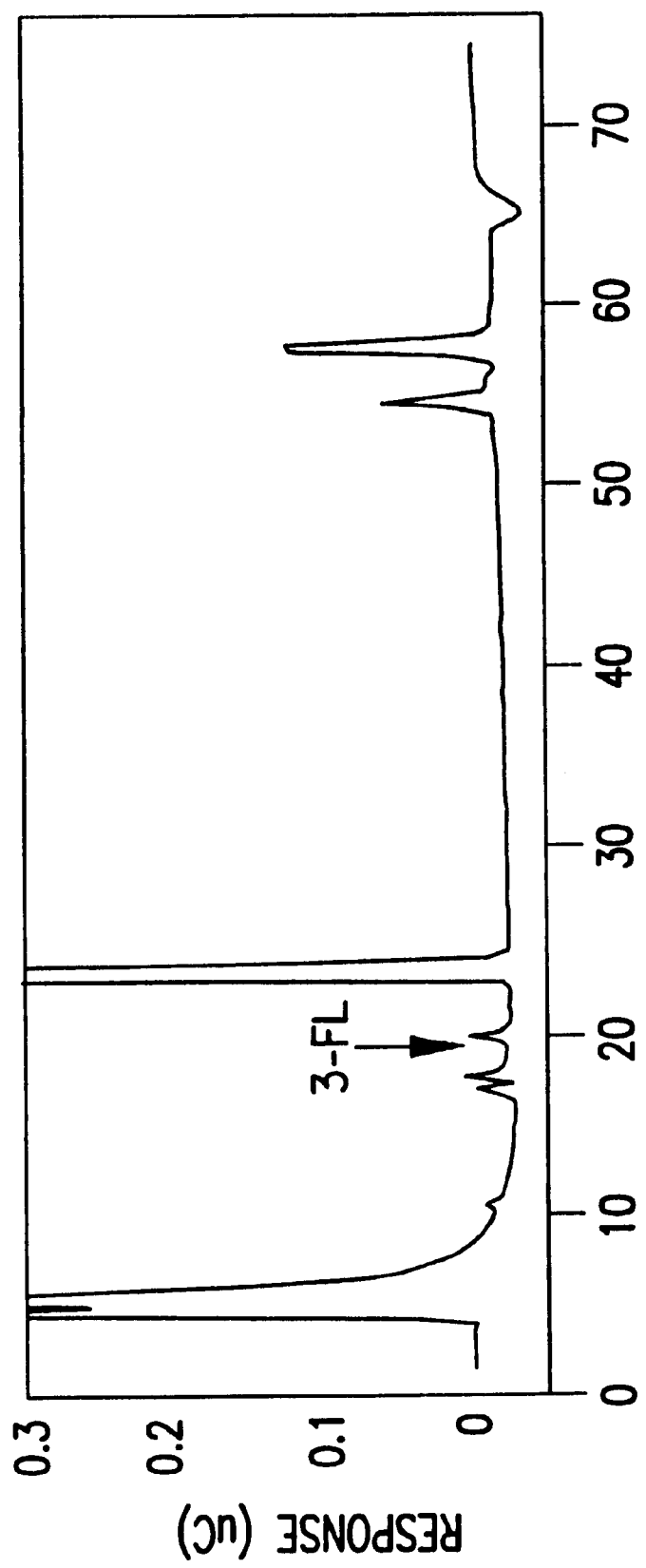
FIGS. 14–16 relate to a method of expressing an enzyme (i.e., human fucosyltransferase IV) using heterologous lactogenically induced transgenic expression.
Figure 14C:
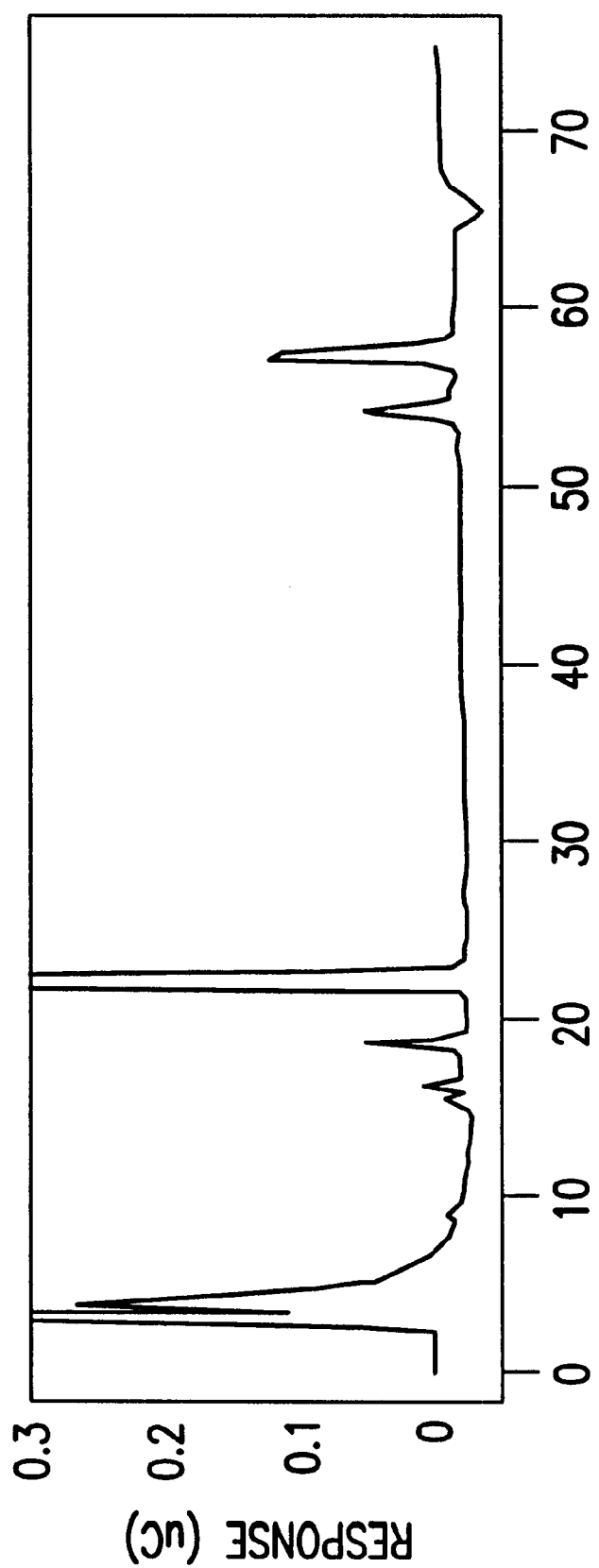

The results of the above procedures were as follows:

FIG. 14 shows chromatograms for control and transgenic milk oligosaccharide extracts (Panels A and B, respectively). It can be clearly observed that a peak signal was generated by milk obtained from an animal transfected with the fucosyltransferase FucT-IV, while there was only a trace in the non-transgenic control animal milk. Additionally, material shown in Panel B was spiked with authentic 3-fucosyllactose to determine if the neooligosaccharide present in milk of the transgenic animal was indeed 3-fucosyllactose (Panel C). The elution of this carbohydrate is further consistent with the independent elution of authentic 3-fucosyllactose indicated by the arrow in Panel B.

Figure 15:
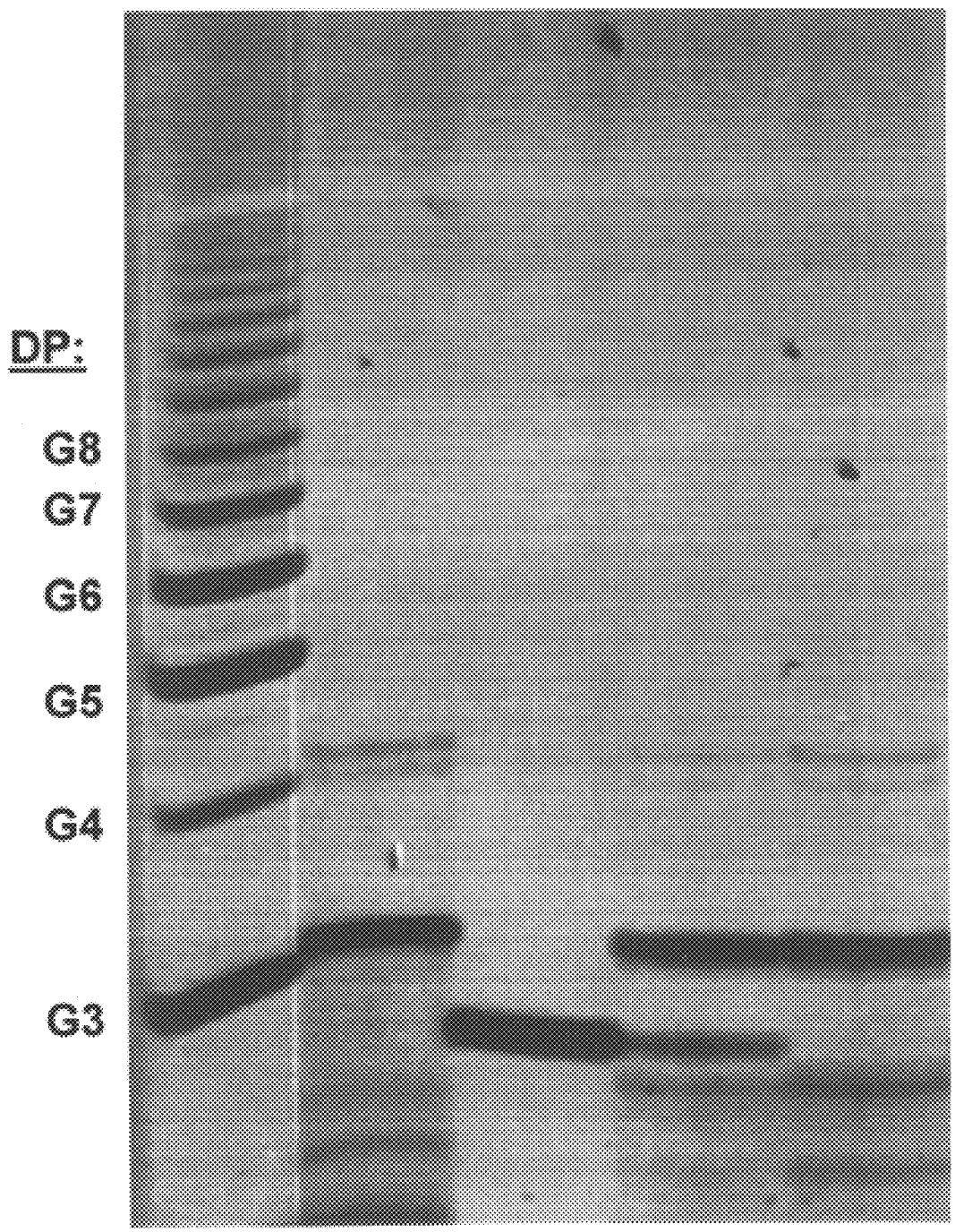

Additionally, oligosaccharide extracts from control and transgenic animals were separated into neutral oligosaccharides and sialyoligosaccharides or negatively charged structures. This allowed for simpler images when labeled oligosaccharides where resolved by gel electrophoresis. FIG. 15 is the image of a gel used to resolve neutral labeled oligosaccharides. (Lane 1 is a labeled starch hydrolyzate used as a molecular weight standard, lane two is the neutral profile obtained from the milk of a non-transgenic control animal, lane 3 is authentic 3 fucosyllactose, lane 4 is the neutral profile of a transgenic animal expressing FucT-IV and lane 5 is the same material as in lane 4 but after specific fucosidase digestion.) A band which comigrated with authentic 3 fucosyllactose was only clearly visible in the profile from the transgenic sample, and the band disappeared when treated with specific 3-fucosidase. Additionally, the material was not susceptible to hydrolysis by α1-2-fucosidase.

Figure 16A:
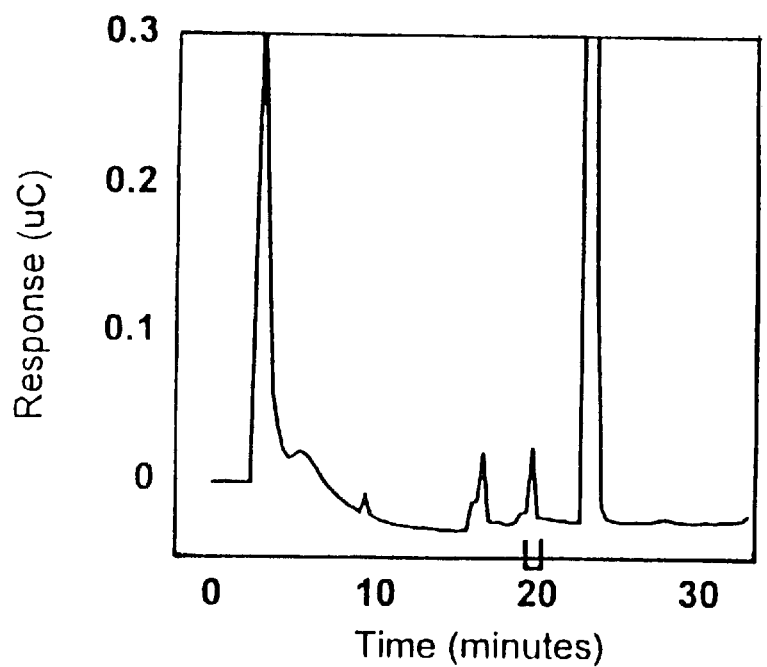
Figure 16B:
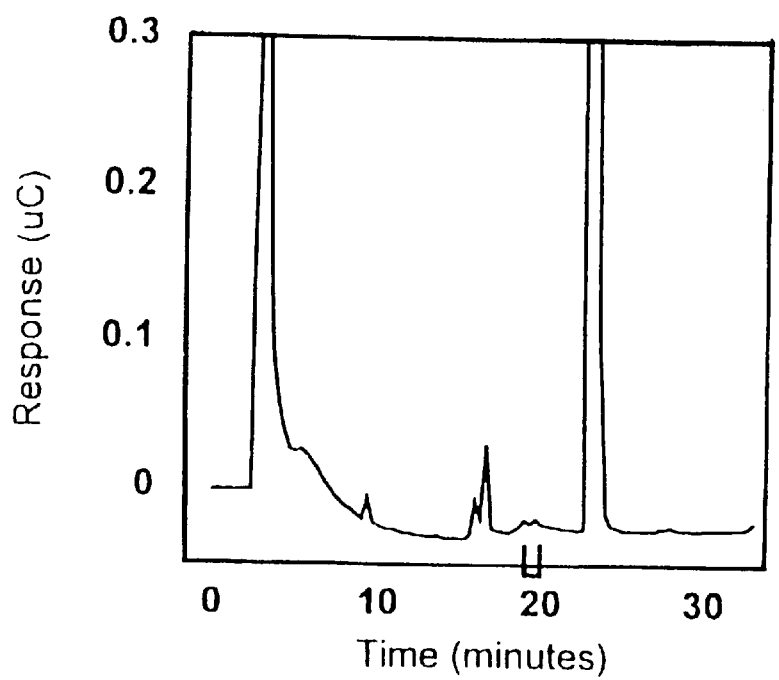
Figure 16C:
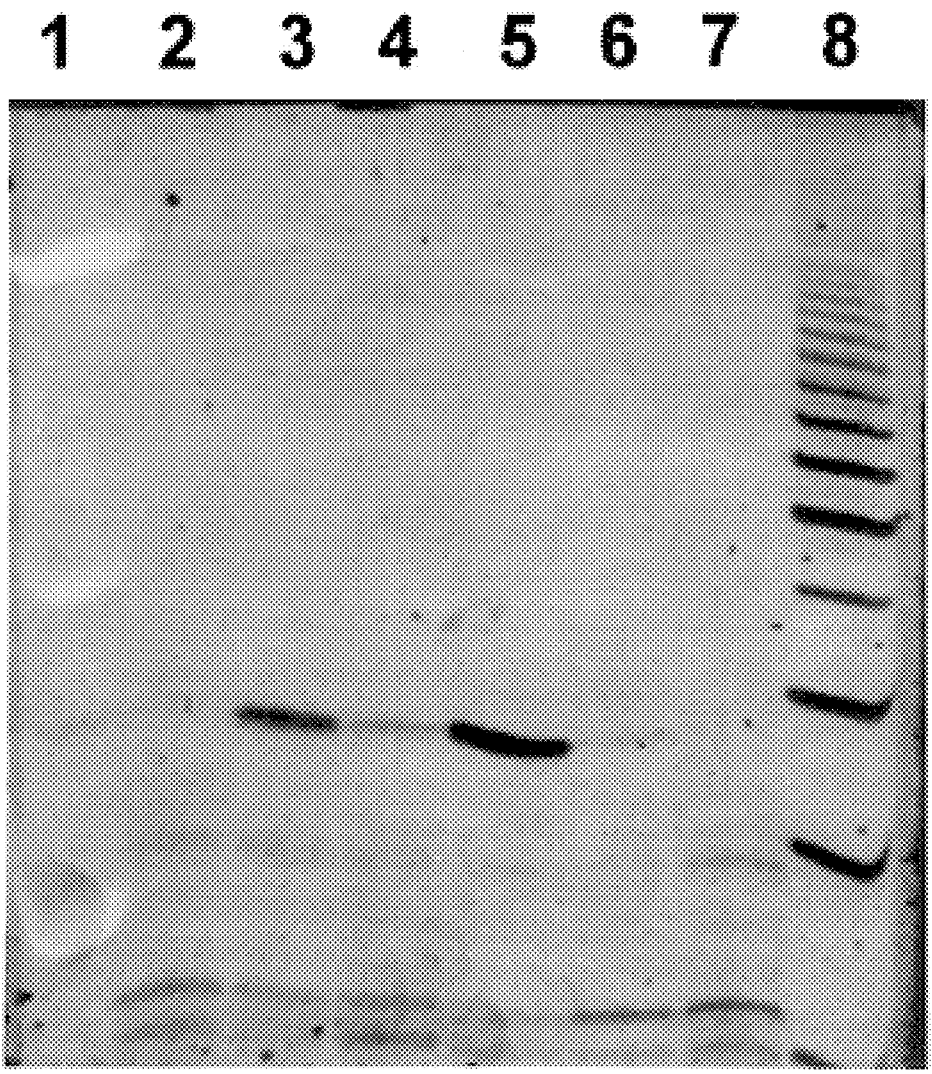

To further characterize the neooligosaccharide, fractions were collected directly from the chromatography eluants. Oligosaccharide extracts were subjected to HPAEC as described above and eluants were collected in fractions. Each fraction corresponded to 0.5 minutes of elution. The collected fractions are indicated by brackets in FIG. 16 Panel A for a transgenic milk sample and Panel B for a non-transgenic control. These fractions were labeled and applied to FACE as indicated in the lane identification legend of the electrophoretogram image in FIG. 16.

Both HPAEC and FACE show that the non-transgenic animal had only traces of an oligosaccharide comigrating with authentic 3 fucosyllactose (Lane 5). However, a fraction from the oligosaccharide extract from the milk sample obtained from a transgenic animal generated a clear signal which comigrated with 3-fucosyllactose. This further supports the concept that 3-fucosyllactose is synthesized by the expression of the transgene.

EXAMPLE IV

Simultaneous Expression of Two Transgenic Fucosyltransferases Through Interbreeding of Two Previously Established Murine Transgenic Lines A female mouse from a stable transgenic line expressing the human fucosyltransferase "H", driven by a lactogenic promoter (Prieto et al., *Journal of Biological Chemistry*, 270:29515–29519 (1995)) was allowed to mate with a male mouse from a stable transgenic line expressing the murine Gal α1-3 transferase, also driven by a lactogenic promoter (see Example I).

The resulting progeny was assessed for the presence of the transgenes, in their genome, utilizing tail biopsies and probing with suitable hybridizing probes. Females deemed to be positive for both transgenes were further mated and pregnancy was allowed to proceed to term. Milk was obtained from one of these females, and the carbohydrate profile was determined by High pH Anion Exchange Chromatography (HPAEC), as described in Examples I and II.

Figure 17:
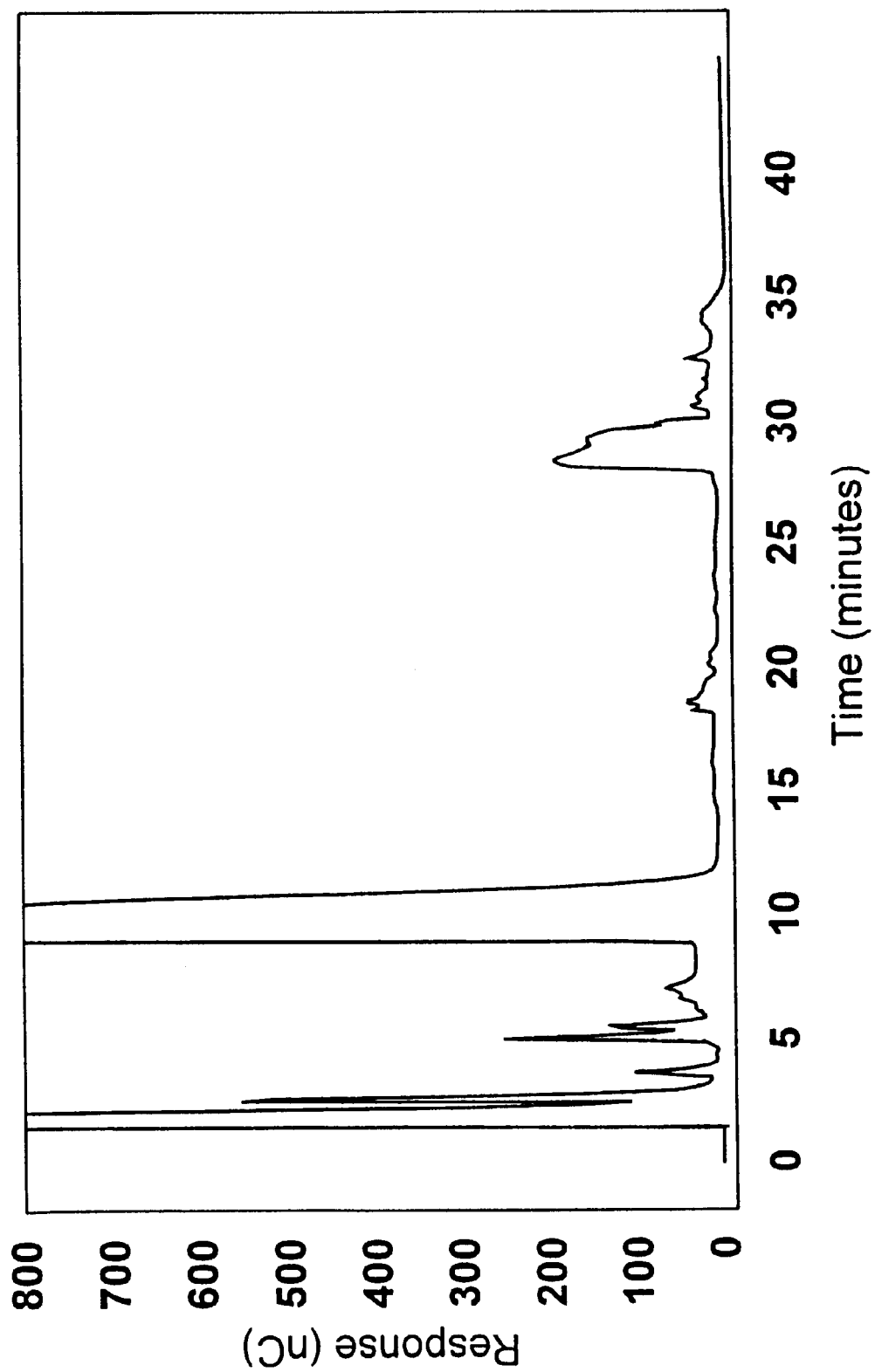
FIGS. 17 and 18 relate to the simultaneous transgenic expression of glycosyltransferases in mice.
Figure 18:
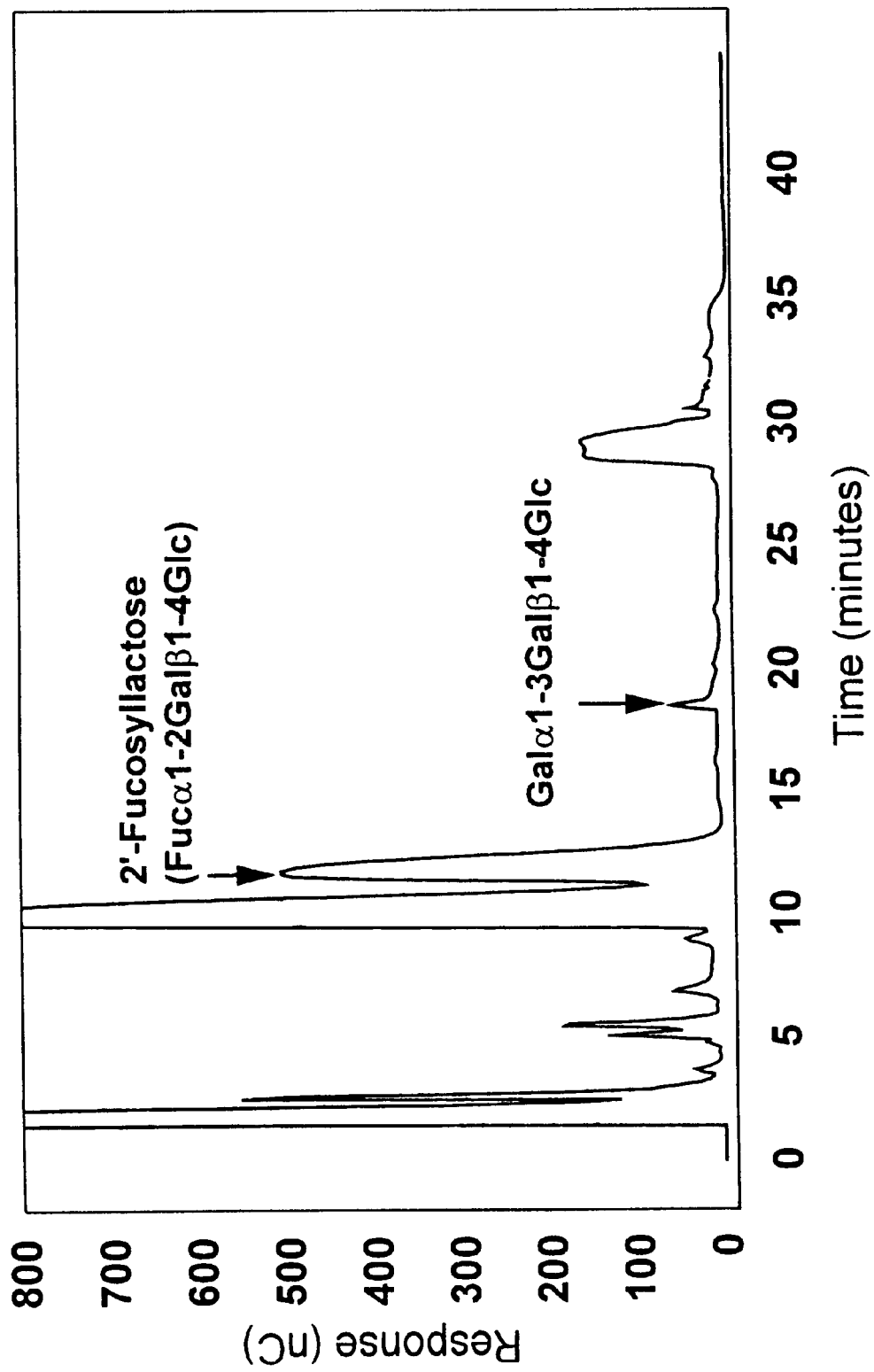

As observed in FIGS. 17 and 18, a major signal can be observed at the elution time of 2'-fucosyllactose while a minor signal can be observed precisely at the elution time of the synthetic trisaccharide Gal α1-3 Galβ1-4Glc. Elution positions of authetic standards are indicated.

In particular, the above results indicate that in order to obtain transgenic animals which produce milk containing complex oligosaccharide and glycoprotein profiles, it is not necessary to start de novo and subsequently inject mice embryos with new glycosyltransferase encoding constructs. Interbreeding of transgenic animals expressing different glycosyltransferases will result in animals that inherit transferases from their parents according to Mendelian genetics. This, in turn, will result in the synthesis of the relevant secondary gene products.

EXAMPLE V

Transgenic Expression of a Bacterial Glycosyltransferase (i.e.. UDP-GlcNAc:Galβ1-4) in Lactating Mammary Glands of Mice A GlcNAc-transferase from *Neisseria polysaccharea* was used. The codon bias of the gene encoding the enzyme was altered to favor the use of codons commonly found in mammalian genes. The "rebiased" gene was used to transfect murine "L" cells commonly used as murine culture cell lines. Once activity is proven in these mammalian cells, the resulting DNA encoding the GlcNAc-transferase was used to prepare a construct amenable for transgenic expression during lactogenesis in mice.

GlcNAc-transferase activity was assessed by a liquid phase synthesis assay. Mouse "L" cells (i.e., a pellet from a petri dish) are resuspended in Phosphate Buffered Saline buffer containing 1 mM CaCl2, 20 mM lactose and 20 mM UDP-GlcNAC. The resulting mixture was sonicated for 5 minutes and incubated overnight at 37 degrees centrigrade. The resulting incubation mixture was then filtered through microcon (Amicon, Beverly, Mass.) centricon (10,000 AMU, MW cutoff) filters, and the filtrate was diluted for HPAEC analysis.

Figure 19:
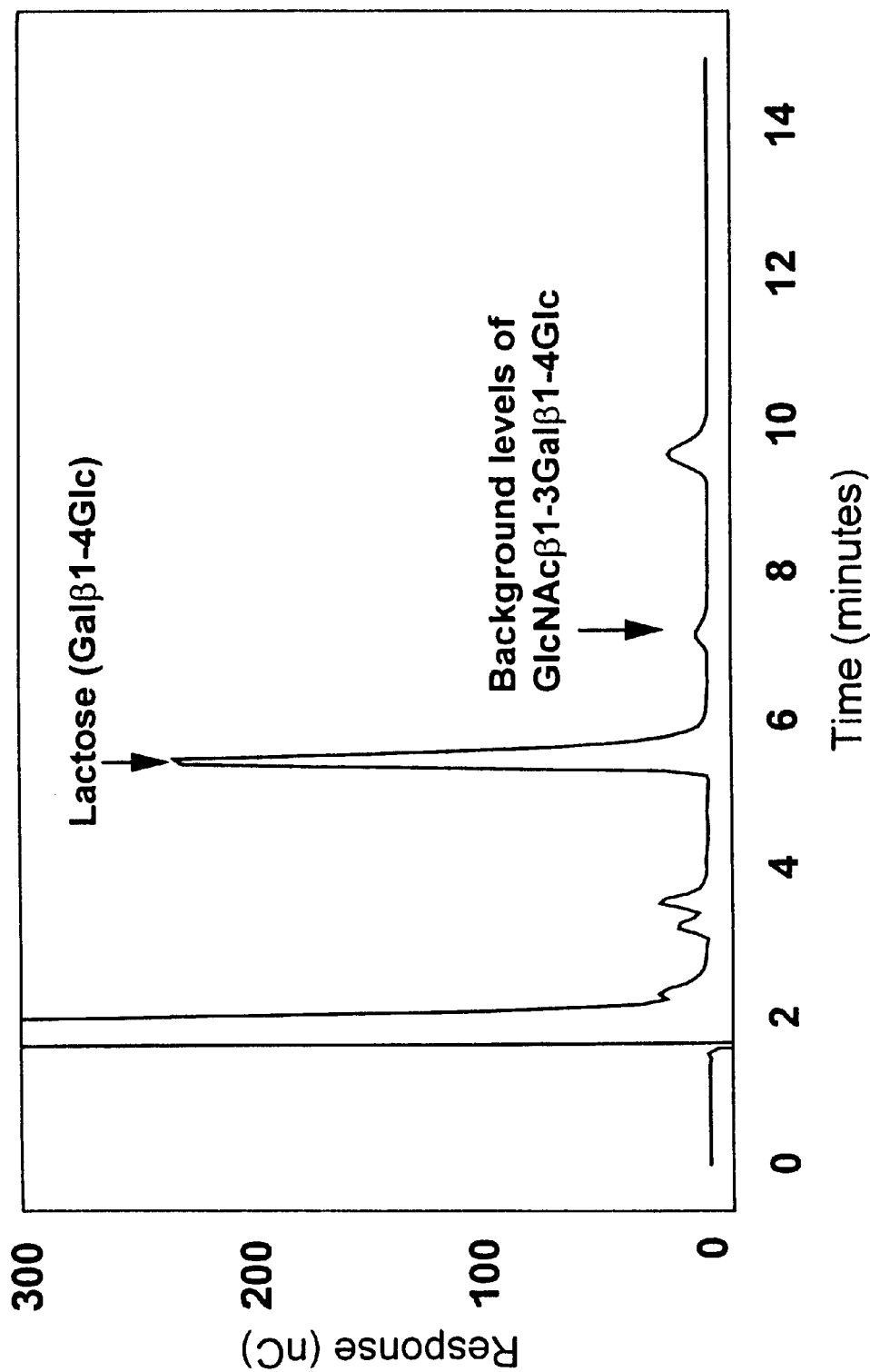
FIGS. 19–21 relate to a method of transgenically expressing a bacterial glycosyltransferase in lactating mammary glands of mice.
Figure 20:
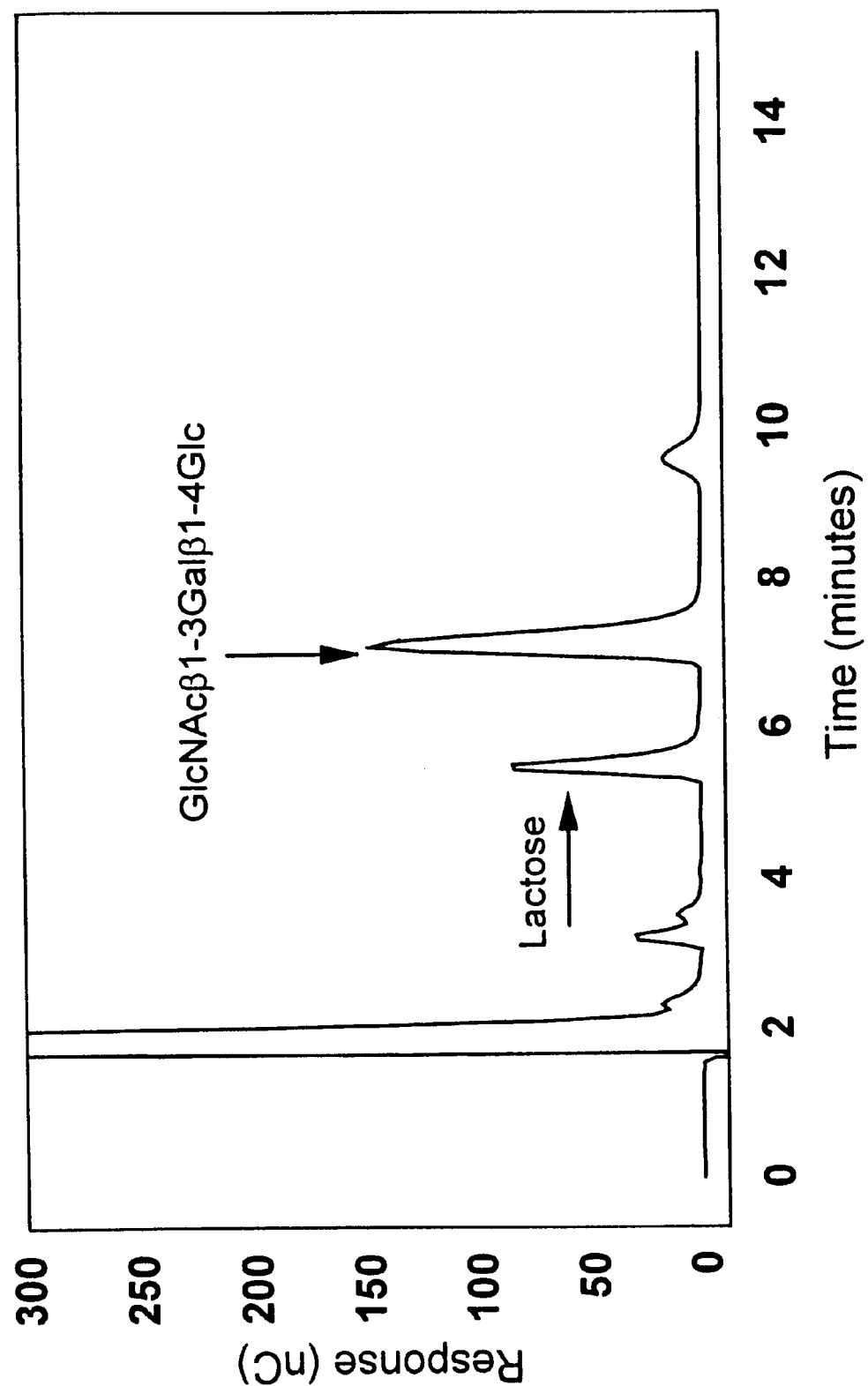
Figure 21:
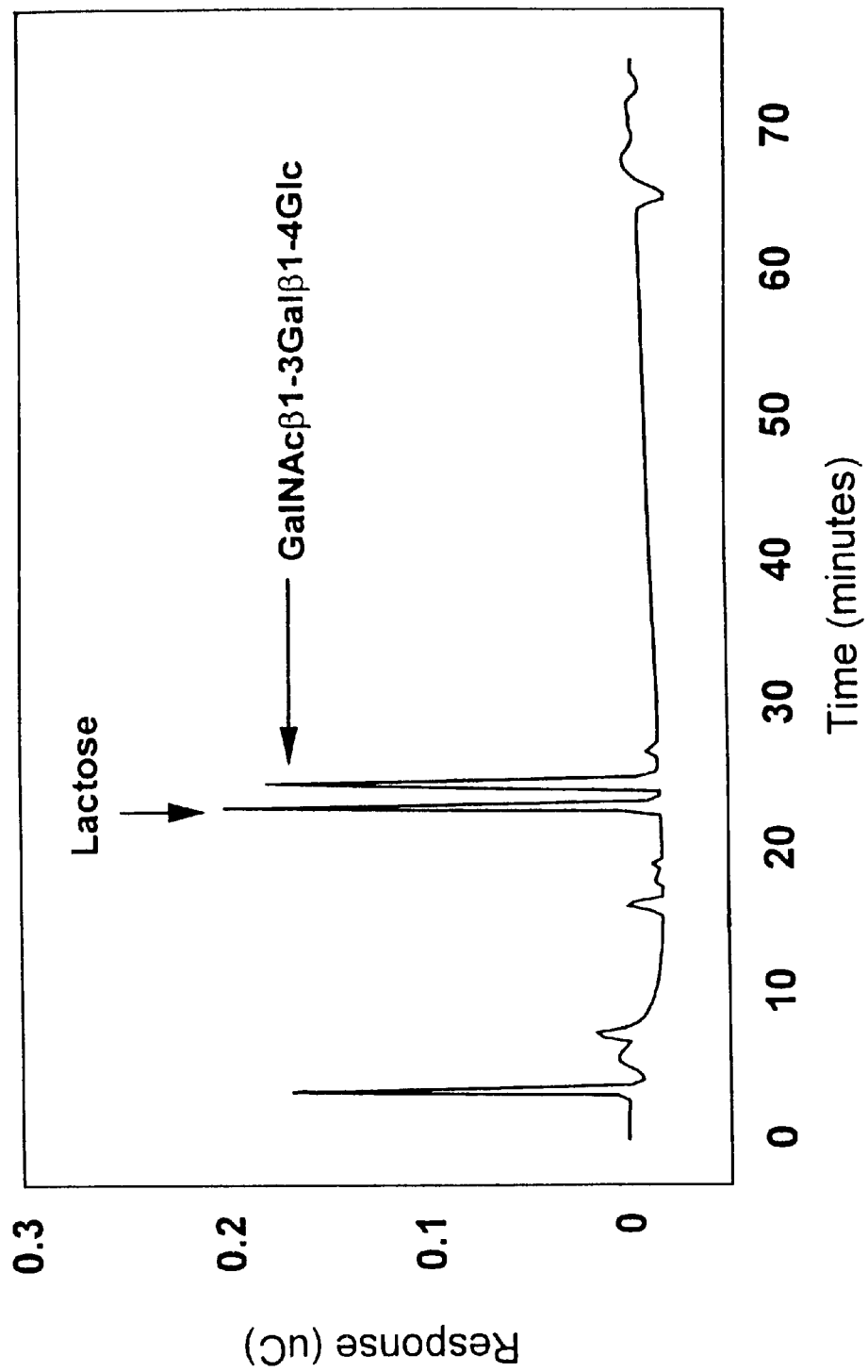

Oligosaccharide extracts were prepared as reported in Example I. FIGS. 19–21 clearly indicate that the bacterial enzyme was successfully expressed in mammalian tissues.

The milk of the transgenic animals may contain the tetrasaccharide lacto-N-neotetraose (NnnT) as a result of the expression of the N-acetyl-glucosaminyl-transferase.

What is claimed is:

1. A non-human, transgenic mammal, wherein the genome of said mammal comprises at least one heterologous DNA sequence encoding an enzyme, wherein said enzyme is a glycosyltransferase operatively linked to a mammary gland-specific promoter, wherein expression of said at least one DNA sequence results in the production of oligosaccharides and glycoproteins in the milk of said mammal.

2. The non-human, transgenic mammal of claim 1, wherein said mammal is selected from the group consisting of a mouse, a rat, a rabbit, a pig, a goat, a sheep and a cow.

3. The non-human, transgenic mammal of claim 1, wherein said glycosyltransferase is selected from the group consisting of a fucosyltransferase, a galactosyltransferase, an acetylase, a glucoronyltransferase, a gluconylepimerase, a sialyltransferase, a mannosyltransferase, a sulfotransferase, a S-acetylgalactosaminyltransferase and a N-acetylglucosaminyltransferase.

4. The non-human, transgenic mammal of claims, wherein said oligosaccharides are selected from the group consisting of galactose α1-3galactose β1-4 glucose, 2'fucosyllactose, 3'fucosyllactose, lacto-N-neo-tetraose, lacto-N-tetraose, lacto-N-fucopentaose, a sialylated derivative of lacto-N-fucopentaose, lacto-N-fucopentaose II, a sialylated derivative of lacto-N-fucopentaose II, lacto-N-fucopentaose III, a sialylated derivative of lacto-N-fucopentaose III, lacto-N-fucopentaose IV, a sialylated derivative of lacto-N-fucopentaose IV, lacto-N-fucopentaose V, a sialylated derivative of lacto-N-fucopentaose V, lacto-N-di-fucopentaose I, a sialylated derivative of lacto-N-di-fucopentaose, lacto-N-di-fucopentaose II, a sialylated derivative of lacto-N-di-fucopentaose II, lacto-N-hexaose, a fucosylated derivative of lacto-N-hexaose, sialyltetrasaccharide a, a fucosylated derivative of sialyltetrasaccharide a, sialyltetrasaccharide b, a fucosylated derivative of sialyltetrasaccharide b, sialyltetrasaccharide c and a fucosylated derivative of sialyltetrasaccharide c.

5. A method for producing a non-human, transgenic mammal whose somatic and germ cells contain at least one transgene, wherein expression of said at least one transgene results in the production of oligosaccharides and glycoproteins in the milk of said mammal, the method comprising the steps of:

(a) preparing at least one transgene, said at least one transgene comprising in operable association 1) at least one expression regulatory sequence functional in mammary secretory cells, 2) a DNA sequence encoding a signal sequence functional in mammary secretory cells, and 3) a DNA sequence encoding an enzyme;

(b) introducing said at least one transgene into a non-human, mammalian embryo, and transferring the resulting embryo into a recipient female;

(c) identifying at least one female offspring, where expression of said at least one transgene results in the production of at least one enzyme which then catalyzes the production of oligosaccharides and glycoproteins in the milk of said mammal, wherein said at least one enzyme is a glycosyltransferase.

6. The method of claim 5, wherein said non-human, transgenic mammal is selected from the group consisting of a mouse, a rat, a rabbit, a pig, a goat, a sheep and a cow.

7. The method of claim 5, wherein said glycosyltransferase is selected from the group consisting of a fucosyltransferase, a galactosyltransferase, an acetylase, a glucoronyltransferase, a gluconylepimerase, a sialyltransferase, a mannosyltransferase, a sulfotransferase, a β-acetylgalactosaminyltransferase and a N-acetylglucosaminyltransferase.

8. The method of claim 5, wherein said oligosaccharides are selected from the group consisting of galactose α1-3 galactose β1-4 glucose, 2'fucosyllactose, 3'fucosyllactose, lacto-N-neo-tetraose, lacto-N-tetraose, lacto-N-fucopentaose, a sialylated derivative of lacto-N-fucopentaose, lacto-N-fucopentaose II, a sialylated derivative of lacto-N-fucopentaose II, lacto-N-fucopentaose III, a sialylated derivative of lacto-N-fucopentaose III, lacto-N-fucopentaose IV, a sialylated derivative of lacto-N-fucopentaose IV, lacto-N-fucopentaose V, a sialylated derivative of lacto-N-fucopentaose V, lacto-N-di-fucopentaose I, a sialylated derivative of lacto-N-di-fucopentaose, lacto-N-di-fucopentaose II, a sialylated derivative of lacto-N-di-fucopentaose II, lacto-N-hexaose, a fucosylated derivative of lacto-N-hexaose, sialyltetrasaccharide a, a fucosylated derivative of sialyltetrasaccharide a, sialyltetrasaccharide b, a fucosylated derivation of sialyltetrasaccharide b, sialyltetrasaccharide c and a fucosylated derivative of sialyltetrasaccharide c.

9. A method of producing milk in a non-human, transgenic mammal, said method comprising the steps of:

(a) preparing at least one transgene, said at least one transgene comprising is operable association 1) a promoter functional in mammary secretory cells, 2) a DNA sequence encoding an enzyme, wherein said enzyme is a glycosyltransferase and wherein expression of said at least one transgene results in production of oligosaccharides and glycoproteins in said milk of said mammal;

(b) inserting said at least one transgene into said non-human, transgenic mammal;

(c) milking said non-human, transgenic mammal in order to obtain said milk, wherein said milk comprises said oligosaccharides and glycoproteins.

10. The method of claim 9, wherein said non-human, transgenic mammal is selected from the group consisting of a mouse, a rat, a rabbit, a pig, a goat, a sheep and a cow.

11. The method of claim 9, wherein said glycosyltransferase is selected from the group consisting of a fucosyltransferase, a galactosyltransferase, an acetylase, a glucoronyltransferase, a gluconylepimerase, a sialyltransferase, a mannosyltransferase, a sulfotransferase, a β-acetylgalactosaminyltransferase and a N-acetylglucosaminyltransferase.

12. The method of claim 9, wherein said oligosaccharides are selected from the group consisting of galactose α1-3 galactose β1-4 glucose, 2'fucosyllactose, 3'fucosyllactose, lacto-N-neo-tetraose, lacto-N-tetraose, lacto-N-fucopentaose, a sialylated derivative of lacto-N-fucopentaose, lacto-N-fucopentaose II, a sialylated derivative of lacto-N-fucopentaose II, lacto-N-fucopentaose III, a sialylated derivative of lacto-N-fucopentaose III, lacto-N-fucopentaose IV, a sialylated derivative of lacto-N-fucopentaose IV, lacto-N-fucopentaose V, a sialylated derivative of lacto-N-fucopentaose V, lacto-N-di-fucopentaose I, a sialylated derivative of lacto-N-di-fucopentaose, lacto-N-di-fucopentaose II, a sialylated derivative of lacto-N-di-fucopentaose II, lacto-N-hexaose, a fucosylated derivative of lacto-N-hexaose, sialyltetrasaccharide a, a fucosylated derivative of sialyltetrasaccharide a, sialyltetrasaccharide b, a fucosylated derivation of sialyltetrasaccharide b, sialyltetrasaccharide c and a fucosylated derivative of sialyltetrasaccharide c.

13. A method for producing oligosaccharides and glycoproteins in the milk of a non-human transgenic mammal, the method comprising the steps of:

(a) preparing at least one transgene, said at least one transgene comprising in operable association 1) at least one expression regulatory sequence functional in mammary secretory cells, 2) a DNA sequence encoding a signal sequence functional in mammary secretory cells, and 3) a DNA sequence encoding an enzyme, wherein said enzyme is a glycosyltransferase;

(b) introducing said at least one transgene into a non-human, mammalian embryo, and transferring the resulting embryo into a recipient female;

(c) identifying at least one female offspring, where expression of said at least one transgene results in the production of at least one enzyme which then catalyzes the production of said oligosaccharides and glycoproteins in the milk of said mammal, wherein said at least one enzyme is a glycosyltransferase;

(d) milking said mammal; and (e) isolating said oligosaccharides and glycoproteins from said milk.

14. The method of claim 13, wherein said non-human transgenic mammal is selected from the group consisting of a mouse, a rat, a rabbit, a pig, a goat, a sheep and a cow.

15. The method of claim 14, wherein said non-human transgenic mammal is a cow.

16. The method of claim 13 wherein said glycosyltransferase is selected from the group consisting of glycosyltransferase is selected from the group consisting of a fucosyltransferase, a galactosyltransferase, an acetylase, a glucoronyltransferase, a gluconylepimerase, a sialyltransferase, a mannosyltransferase, a sulfotransferase, a B-acetylgalactosaminyltransferase and a N-acetylglucosaminyl-transferase.

17. The method of claim 13, wherein said oligosaccharides are selected from the group consisting of galactose a 1-3 galactose β1-4 glucose, 2'fucosyllactose, 3'fucosyllactose, lacto-N-neo-tetraose, lacto-N-tetraose, lacto-N-fucopentaose, a sialylated derivative of lacto-N-fucopentaose, lacto-N-fucopentaose II, a sialylated derivative of lacto-N-fucopentaose II, lacto-N-fucopentaose III, a sialylated derivative of lacto-N-fucopentaose III, lacto-N-fucopentaose IV, a sialylated derivative of lacto-N-fucopentaose IV, lacto-N-fucopentaose V, a sialylated derivative of lacto-N-fucopentaose V, lacto-N-di-fucopentaose I, a sialylated derivative of lacto-N-di-fucopentaose, lacto-N-di-fucopentaose II, a sialylated derivative of lacto-N-di-fucopentaose II, lacto-N-hexaose, a fucosylated derivative of lacto-N-hexaose, sialyltetrasaccharide a, a fucosylated derivative of sialyltetrasaccharide a, sialyltetrasaccharide b, a fucosylated derivation of sialyltetrasaccharide b, sialyltetrasaccharide c and a fucosylated derivative of sialyltetrasaccharide c.

18. The method of claim 13, wherein said glycoproteins are human milk proteins.

* * * * *